US005883153A

United States Patent [19]

Roberts et al.

[11] Patent Number: 5,883,153
[45] Date of Patent: Mar. 16, 1999

[54] FLUORIDE ION SUSTAINED RELEASE PREFORMED GLASS IONOMER FILLER AND DENTAL COMPOSITIONS CONTAINING THE SAME

[75] Inventors: Thomas Arwel Roberts, Congleton, United Kingdom; Kozo Miyai, Nara, Japan; Kunio Ikemura, Joyo, Japan; Kiyomi Fuchigami, Kyoto, Japan; Toshio Kitamura, Uji, Japan

[73] Assignee: Shofu Inc., Kyoto, Japan

[21] Appl. No.: 892,766

[22] Filed: Jul. 15, 1997

Related U.S. Application Data

[63] Continuation of Ser. No. 525,662, filed as PCT/JP94/00620 Apr. 14, 1994, published as WO94/23687 Oct. 27, 1994, abandoned.

[30] Foreign Application Priority Data

Apr. 15, 1993 [GB] United Kingdom ................ 9307777.4

[51] Int. Cl.⁶ ................ A61K 6/08; C08K 3/34
[52] U.S. Cl. .................. 523/116; 523/117; 523/212; 524/443; 524/556; 524/450; 524/845; 524/847; 524/916; 501/151
[58] Field of Search ..................... 523/116, 117; 524/443, 556, 916, 845, 847; 501/151

[56] References Cited

U.S. PATENT DOCUMENTS

| | | |
|---|---|---|
| 3,814,717 | 6/1974 | Wilson et al. . |
| 4,089,830 | 5/1978 | Tezuka et al. . |
| 4,376,835 | 3/1983 | Schmitt et al. . |
| 4,435,380 | 3/1984 | Pader . |
| 4,599,228 | 7/1986 | Ladanyi . |
| 4,599,363 | 7/1986 | Miles, Jr. et al. . |
| 4,629,746 | 12/1986 | Michl et al. . |
| 4,758,612 | 7/1988 | Wilson et al. . |
| 4,808,228 | 2/1989 | Randklev ................ 523/116 |
| 4,814,362 | 3/1989 | Billington et al. . |
| 4,872,936 | 10/1989 | Engelbrecht . |
| 4,892,725 | 1/1990 | Amjad . |
| 4,900,697 | 2/1990 | Akahane et al. . |
| 5,063,257 | 11/1991 | Akahane et al. . |
| 5,130,347 | 7/1992 | Mitra . |
| 5,151,453 | 9/1992 | Ibsen et al. . |

FOREIGN PATENT DOCUMENTS

| | | |
|---|---|---|
| 0356868 | 3/1990 | European Pat. Off. . |
| 0363903 | 4/1990 | European Pat. Off. . |
| 0442326 | 8/1991 | European Pat. Off. ........... 523/116 |
| 3-47107 | 2/1981 | Japan . |
| 57-75908 | 5/1982 | Japan . |
| 58-99406 | 6/1983 | Japan . |
| 1-308855 | 12/1989 | Japan . |
| 2-164807 | 6/1990 | Japan . |

*Primary Examiner*—Andrew E.C. Merriam
*Attorney, Agent, or Firm*—Stevens, Davis, Miller, & Mosher, L.L.P.

[57] ABSTRACT

There is provided a fluoride-ion sustained release preformed glass ionomer filler comprising a powdery reaction product of polyalkenoic acid with a fluorine-containing glass, and a method of producing the same. There is also provided a dental composition containing the filler. The fluoride-ion sustained release pre-formed glass ionomer filler is long capable of releasing fluoride ions in the presence of water without involving disintegration. The dental composition of the invention is useful particularly for prevention of dental caries and like trouble.

31 Claims, 1 Drawing Sheet

FLUORIDE ION SUSTAINED RELEASE PREFORMED GLASS IONOMER FILLER AND DENTAL COMPOSITIONS CONTAINING THE SAME

This application is a Continuation of application Ser. No. 08/525,662, filed Sep. 29, 1995, now abandoned which in turn is a 371 Application of International Application PCT/JP94/00620, filed Apr. 14, 1994 published as WO94/23687 Oct. 27, 1994.

TECHNICAL FIELD

The present invention relates to fluoride-ion releasable pre-formed glass ionomer fillers. More particularly, the invention relates to a pre-formed glass ionomer filler capable of stable and sustained fluoride ion release without involving elution and disintegration, and dental compositions containing the same.

The pre-formed glass ionomer filler in accordance with the present invention is useful mainly for the preparation of dental compositions. Additionally, because of its sustained fluorine releasability feature, the pre-formed glass ionomer filler is also useful for hard tissues of a living body which take in fluorine, including teeth and bones in particular and, therefore, it is applicable for use in various fields, such as surgery, orthopaedic surgery, and plastic surgery, as well as in dentistry.

BACKGROUND ART

Fluoride ion fluorinates the hydroxyapatite of dentin and thus strengthen the dentin. Therefore, fluoride ion has much to be expected of for use in inhibiting or preventing dental caries. Further, it is conceivable to use fluoride ions in combination with calcium ion and phosphoric ion for capping dental tuble, calcification thereof, and/or recalcification of softened dentin, through which much can be expected for protection of dental pulp and otherwise.

Hitherto, in the field of dentistry, for the purpose of preventing dental caries, as well as inhibiting secondary dental caries, there have been used fluoride-ion releasable compounds, such as sodium fluoride, potassium fluoride, aluminum fluoride, sodium monofluorophosphate, strontium fluoride, zinc fluoride, primary tin fluoride, and fluorides of rare earth elements. Dental compositions containing such compounds are also known.

Primarily, however, liberation of fluoride ions is a dissociation of the fluoride ions in the presence of water and often involves an elution, i.e., dissolution, of a compound, which in effect means a disintegration of a composition and, in addition, the presence of counter ions. Therefore, the above noted known compounds are unstable for use in dental compositions.

In the mean while, cements formed by the reaction of glass with an ionomer are well known as a dental composition which is releasable fluoride ion, and have many uses in dentistry, for example, the restoration of cavities or lesions, sealing or filling occlusal pits and fissures, sealing root surfaces for overdentures or for luting.

These ionomer cements are hydrogel salts that are formed by the reaction between a basic calcium aluminofluorosilicate glass and an acidic polyelectrolyte which is a homopolymer or a copolymer of unsaturated carboxylic acid. Cements of this type are particularly preferred as dental cements because they are highly biocompatible, bond strongly to the tooth structure and allow fluoride to be released. However, the setting reaction between the glass and the ionomer is slow and therefore the length of time required for the cement to set to a sufficient hardness for the dentist to perform the necessary finishing presents a problem.

Dental cements have also been proposed which contain a filler and a light-curable resin, so that the setting of the cement is effected by its exposure to light. In one embodiment the filler is glass and the resin is chosen to be an ionomer which reacts with the glass and is also light-curable. The time that is required for the cement to reach the required hardness is thereby reduced. This improvement has provided significant improvements over the traditional glass ionomer cements. However, these light-curable compositions have the disadvantages that only a limited range of monomers can be used. This is because they must be both ionomeric and light-curable.

Moreover, in order that the dentist can use the cement, it is essential that it does not set until after it has been placed in the tooth. The glass and the ionomer are therefore commonly supplied separately in the form of a powder and a liquid respectively. The dentist must then mix them in the appropriate ratio immediately prior to application to the tooth. As the setting process commences on contact between the ionomer and the glass, the dentist must work quickly to mix the cement and to apply it to the tooth. The cement is then set by exposing to a light. In general, setting is accelerated by exposing the cement to a bright light.

The drawbacks of this method are that it is difficult to get the ratio between the components correct and to achieve efficient mixing. These drawbacks result in variations in the composition of the final cement.

There is also a danger that during mixing air bubbles will be introduced into the mixture which will lead to weakness in the final cement. A further difficulty in achieving a product having the correct ratio of glass to ionomer is that the components are highly temperature and humidity sensitive and results may therefore vary from day to day.

In an attempt to overcome these drawbacks, the powder and liquid are sometimes provided in a single capsule where they are separated by a membrane. Immediately prior to use, the capsule is placed in a machine which pierces the membrane and vibrates the capsule to mix the components. The mixture is then applied to the tooth and cured by exposure to light. Whilst this procedure may overcome the mixing difficulties of the two-pack system described above, the cement provided in the capsule still has the drawback that setting commences immediately the components are mixed.

Accordingly, it is an object of the invention to provide a filler composition which eliminates aforesaid problems, and which is capable of stable and sustained fluoride ion release without involving elution and is not liable to disintegrate a compound. It is another object of the invention to provide dental compositions containing the filler and, more particularly, a light curable one-pack type dental cement.

DISCLOSURE OF INVENTION

The present invention relates to a fluoride ion sustained release pre-formed glass ionomer filler comprised of a powder-form reaction product of polyalkenoic acid and a fluorine-containing glass, and also to a method for production of the same. In particular, the invention relates to a fluoride ion sustained release pre-formed glass ionomer filler in which the powder-form reaction product is a xerogel resulting from dehydration of a gel. Further, the invention relates to a fluoride-ion sustained release pre-formed glass ionomer filler in which the mixing ratio of the polyalkenoic acid to the fluorine-containing glass is from 0.0005:1 to 10:1. The pre-formed glass ionomer filler of the invention exhibits good and sustained fluoride ion releasability without involving disintegration of a compound. Therefore, it can be suitably incorporated into dental compositions or the like which require fluorine release so as to meet needs in a wide range of applications.

The present invention relates to a dental composition containing the fluoride-ion sustained release pre-formed glass ionomer filler. Through addition of the fluoride-ion releasable pre-formed glass ionomer filler of the invention it is no longer necessary to depend for curing of a dental composition upon a reaction between glass and ionomer, and this enables the provision of dental compositions using wide varieties of resins and cements.

As a dental composition in accordance with the invention there is provided a dental composition which comprises a resin composition made of (a) a radical polymerizable compound and (b) a curing agent, and the above mentioned pre-formed glass ionomer filler. In particular, where the resin composition is a light-curable composition comprised of a radical polymerizable compound and a light cure catalyst, the dental composition of the invention may be presented as a one-pack light curable cement that requires no mixing right before use. This eliminates various prior art problems, such as curing in storage, cure delay within mouth, non-uniformity of cement composition, and air bubble inclusion in a cement mass. Another advantage is that the dental composition exhibits better fluoride ion releasability than any conventional glass ionomer cement.

The invention provides a dental composition which contains a pre-formed glass ionomer filler of the invention together with a conventional dental inorganic cement powder and a conventional dental inorganic cement liquid. By adding the pre-formed glass ionomer filler of the invention to such known cement it is possible to improve handling and performance characteristics of the cement.

The present invention further provides a dental composition which comprises a fluoride-ion releasable pre-formed glass ionomer filler of the invention contained in water or in an organic liquid medium. The pre-formed glass ionomer filler of the invention will quickly release fluoride ions in the presence of water and is therefore capable of imparting good fluoride ion release performance to conventional mouth-cleaning compositions, such as mouth rinsing agents and tooth pastes.

BEST MODE FOR CARRYING OUT THE INVENTION

Figure 1:
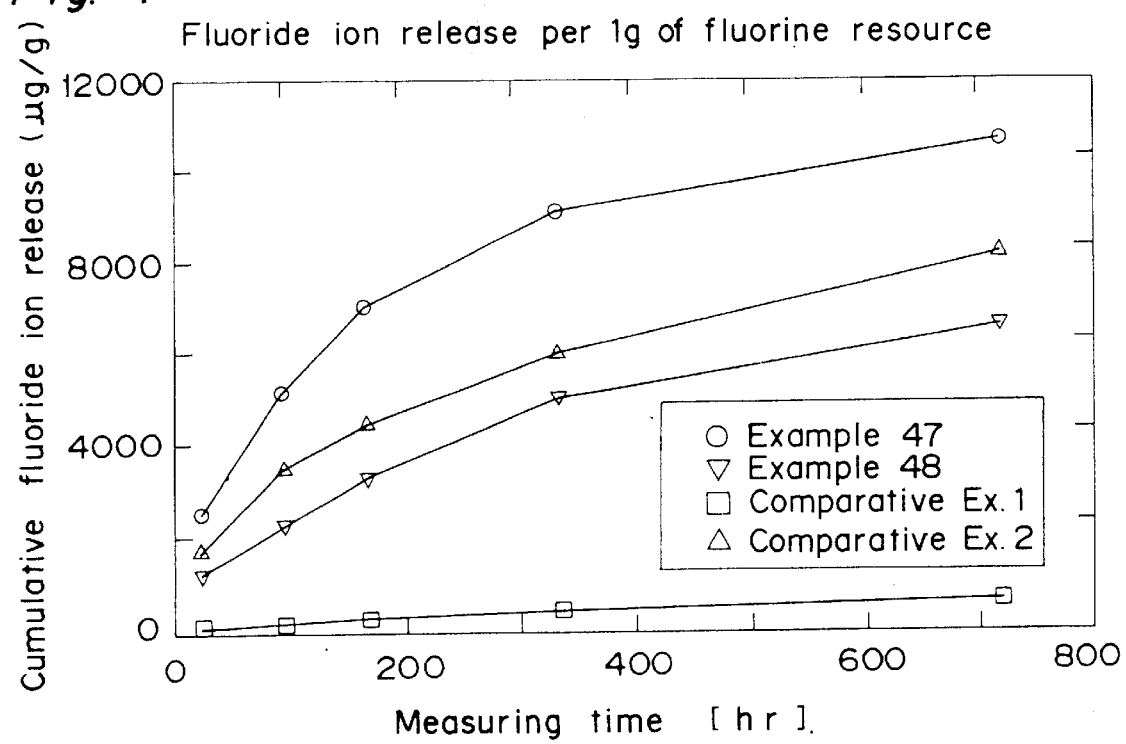
FIG. 1 is a graph showing the results of EXAMPLE 47.

With attention directed to the best utilization of the fluoride-ion sustained release of glass ionomer cement, the present inventors have developed this invention. In accordance with the present invention there is provided a fluoride-ion releasable pre-formed glass ionomer filler comprised of a powdery reaction product of a fluorine-containing glass with polyalkenoic acid.

The fluoride ion release performance of the pre-formed glass ionomer filler of the invention is largely influenced by the composition of the glass used as raw material. The term "glass" used herein means a supercooled mixture of oxides which usually takes the form of a glass containing silica in combination with alumina.

As fluoride containing glasses which are suitable for use in the composition of the present invention may be used those which are conveniently used in glass ionomer cements.

Typical formulations are:

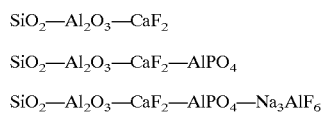

The $Al_2O_3/SiO_2$ molar ration of the glass should preferably be less than 1:1. This ratio provides a cement having optimum properties.

In one embodiment, the glasses may be prepared from a mixture of alumina, silica aluminum fluoride and calcium fluoride and optionally aluminum phosphate and cryolite (sodium aluminum fluoride).

The mixture used preferably has the following composition:

| | | |
|---|---|---|
| calcium oxide | (CaO) | 5–40% by molar |
| silica | ($SiO_2$) | 15–70% by molar |
| alumina | ($Al_2O_3$) | 10–50% by molar |
| sodium oxide | ($Na_2O$) | 0–7% by molar |
| phosphorus pentoxide | ($P_2O_5$) | 0–7% by molar |

The amount of fluoride in these glasses is preferably 5 to 60% by molar.

Whilst the above compositions refers to calcium oxide it is understood that any alkaline earth metal oxide can be used.

These glasses are generally known as alkaline earth metal aluminofluorosilicate glasses. At least a part of the alkaline earth metal may be replaced by lanthanide metals such as lanthanum, gadolinium or ytterbium. Further, a part or all of the alumina in these glasses may be replaced by an oxide of a Group III metal other than aluminum. Likewise a part of the silica in these glasses can be replaced by zirconium oxide or titanium oxide.

If these glasses include strontium, lanthanum, gadolinium, ytterbium or zirconium, they achieve radiopacity. It is preferable that more than 10 wt % of radiopaque element is contained in the glass ionomer filler of the present invention.

The fluoride containing glass used in the present invention may be formed by any conventional manner, such as by melting process or sol-gel process. While the glass may be formed by any conventional manner, in a preferred embodiment the glass may be formed by a sol-gel process in which, for example, a first solution comprising a soluble aluminum compound and a soluble silicon compound is combined with a second solution comprising a soluble compound of a Group II metal. The resultant gel can be recovered in a dry form by heat-drying or by freeze-drying. Using this method means that the additives commonly used in glass production, such as fluxing agents, can be avoided and lower temperatures can be used. Thus a clearer glass can be obtained than heretofore.

Other compounds, such as organo-metallics or alcoholic solutions of inorganic salts, may be added at the sol stage to give a binary or ternary glass.

Acidic or basic catalysts may be added to the sol-gel reaction mixture to enhance gelling rates. Once gelled, the gels are dried to remove residual solvents. They may also be densified at relatively low temperatures, such as 400° C. This process results in an homogenous refractory glass at relatively low temperatures.

This method is particularly suitable for forming glasses incorporating gadolinium and for five component glasses such as:

$$X_nO_m\text{—}CaO\text{—}Al_2O_3\text{—}SiO_2\text{—}F$$

where $X_nO_m$ is an oxide of a radiopaque element X. Such five component glasses are difficult to prepare. However, the sol-gel method enables the glass to be readily formed from the following reagents:

$CaCO_3$ dissolved in HCl as a source of CaO

Aluminum-sec-butoxide (Asb) in iso-butyl alcohol and ethanol as a source of $Al_2O_3$ Tetraethylorthosilicate as a source of $SiO_2$ 40% Hydrofluoric acid as a source of F $Gd(NO_3)_3$ which is readily soluble in ethanol as a source of $Gd_2O_3$ $Sr(NO_3)_2$ which is readily soluble in ethanol as a source of SrO The Asb can be substituted by $Al_2(NO_3).9H_2O$ in ethanol or in methanol. In addition, the calcium oxide can be substituted by a solution of anhydrous $Ca(NO_3)_2$ dissolved in ethanol at 50° C. These solutions are mixed with stirring at 50° C. This may be followed by refluxing at 70° C. After drying, the material is milled while soft and then dried at a temperature of from 400° C. to 500° C. It can then be further milled to the required size.

The fluoride containing glass used in the present invention may also be formed by conventional melting process.

Some compositions of suitable glasses are set out in Table 1. The percentages quoted are those obtained when the resultant glass is analyzed.

methacrylate, or itaconic acid. Also, known polyalkenoic acids having an unsaturated group in a side chain which have been used in light-curable glass ionomer cements may be advantageously used.

Useful polyalkenoic acids in the invention have, in the case of polyacrylic acid, for example, a molecular weight of from 1500 to 150000, preferably from 3000 to 70000, more preferably from 3000 to 30000. If the molecular weight of the polyalkenoic acid is excessively large, gelation precedes the reaction of the acid with the fluorine-containing glass, which is undesirable because the gelation hinders a smooth progress of reaction.

The mixing ratio of the polyalkenoic acid to the fluorine-containing glass is from 0.0005:1 to 10:1, preferably from 1:3 to 3:1. If the mixing ratio of the polyalkenoic acid to the fluorine-containing glass is not within the range of from 1:3 to 3:1, either base or acid is proportionally excessive, and some amount thereof will remain in the resulting filler. In effect, this results in the production of a filler reactive with a dental inorganic cement powder material or dental liquid cement material. However, if the amount of polyalkenoic acid is proportionally larger than the ratio of 10:1, there will be an excessive amount of residual polyalkenoic acid, which is undesirable. If the proportion of the glass is greater than 0.0005:1, there will be an excessive residue of glass core, which is undesirable because the fluoride ion releasability of the filler is considerably reduced.

When a fluorine-containing glass is caused to react with polyalkenoic acid in the presence of water, usually a product in the form of gel is obtained. The pre-formed glass ionomer filler of the invention is preferably a xerogel or a material such that the gel obtained has been dehydrated and dried.

The pre-formed glass ionomer filler of the invention is preferably porous and has a total pore volume of 0.04 to 2.0 cc/g, preferably 0.04 to 1.5 cc/g, more preferably 0.08 to 1.2 cc/g. The pore volume is adjustable by suitably selecting the

TABLE 1

| | Formulation of glass (wt %) | | | | | | | | | | |
|---|---|---|---|---|---|---|---|---|---|---|---|
| | $SiO_2$ | $Al_2O_3$ | SrO | CaO | $La_2O_3$ | $Gd_2O_3$ | $Yb_2O_3$ | $Na_2O$ | $P_2O_5$ | F | $ZrO_2$ |
| G1 | 33.9 | 28.6 | — | 15.9 | — | — | — | — | — | 21.6 | — |
| G2 | 32.5 | 27.3 | — | 15.1 | — | — | — | — | 4.6 | 20.5 | — |
| G3 | 34.5 | 28.3 | — | 11.7 | — | — | — | 2.3 | 6.6 | 16.6 | — |
| G4 | 32.3 | 27.2 | — | 15.0 | — | — | — | — | — | 25.5 | — |
| G5 | 30.0 | 25.3 | 25.8 | — | — | — | — | — | — | 18.9 | — |
| G6 | 24.8 | 21.0 | — | 13.9 | — | 22.4 | — | 2.3 | 2.3 | 13.3 | — |
| G7 | 25.4 | 21.5 | — | 14.2 | 20.6 | — | — | 2.3 | 2.4 | 13.6 | — |
| G8 | 27.8 | 18.8 | — | — | 39.2 | — | — | — | — | 14.2 | — |
| G9 | 25.1 | 17.3 | — | — | — | — | 43.9 | — | — | 13.1 | — |
| G10 | 19.0 | — | — | 8.8 | — | 57.2 | — | — | — | 15.0 | — |
| G11 | 20.5 | 19.9 | 10.2 | — | 25.5 | — | — | — | — | 14.9 | — |
| G12 | 24.6 | 27.7 | — | 15.3 | — | — | — | — | — | 15.6 | 16.8 |

The polyalkenoic acid used in the pre-formed glass ionomer filler of the invention is a homopolymer or copolymer of an unsaturated compound having in a side chain a repeat unit, such as carboxyl group, phosphoric group, or sulfonic group. The polyalkenoic acid reacts with glass to form a glass ionomer.

Homopolymers and copolymers of unsaturated mono-, di-, and tri-carboxylic acids which have in a side chain a carboxyl group are particularly preferred. Specifically, as such homopolymers or copolymers may be exemplified those containing repeat units derived from acrylic acid, maleic acid, crotonic acid, cinnamic acid, 3-butene-1,2,3 tricarboxylic acid, tricarballylic acid, 2-hydroxyethyl composition of the glass, kind of polyalkenoic acid, polymerization degree, and reaction and drying conditions.

The fluoride-ion sustained release pre-formed glass ionomer filler of the invention has a particle size of 0.01 to 100 μm, preferably 0.05 to 30 μm, more preferably 0.1 to 10 μm. If the particle size of the filler is more than 100 μm, there will occur some property degradation when the filler is added to a dental composition. A particle size of less than 0.01 μm is undesirable because it makes the process of pulverizing substantially difficult and is likely to cause agglomeration of particles.

In accordance with the invention, the fluoride-ion sustained release pre-formed glass ionomer filler is produced by causing the polyalkenoic acid to react with the fluorine-containing glass in the presence of a suitable quantity of water, and drying and pulverizing the resulting reaction product as required. Preferably, the reaction is carried out in the presence of excess amount of water. The mixing ratio of water/(fluorine-containing water and polyalkenoic acid) is 0.1 to 10, preferably 0.2 to 7.5. Any insufficiency in the amount of water is undesirable because gelation precedes reaction or there will occur a glass residue in the form of a core.

The process of reaction of the polyalkenoic acid with the fluorine-containing glass may be carried out in a conventional reactor, or in such a reactor as autoclave which is capable of being pressurized or heated up. The reaction is preferably carried out within a temperature range of from ordinary temperature to 70° C. Under inert conditions, however, the temperature may be raised to about 150° C.

Reaction time may be determined on the basis of the quantity of acid groups in the reaction system, though it may sometimes extend over a period of several hours to several days. With the pre-formed glass ionomer filler of the invention, cure reaction is carried out not within an oral cavity, which involves less requirement for cure time reduction. However, in case that a reaction time extending over tens of hours is required, it is desirable to add a chelating agent for cure time adjustment as in the case of cure reaction with a conventional dental glass ionomer cement. For the chelating agent, polybasic acids in general use, such as citric acid and tartaric acid, are advantageously used.

Reaction between the polyalkenoic acid and the fluorine-containing glass is preferably carried out in such a manner that the content of the reactor is in an agitatable state at the beginning of reaction and is in a loose gel form state, e.g., in a yoghurt-like or gruel-like condition, when the process of reaction is nearly completed.

For the production of the fluoride-ion sustained release pre-formed glass ionomer filler of the invention, the following three methods are particularly preferred.

The first method is a method as conventionally employed for the production of glass ionomer cements, which comprises causing the fluorine-containing glass and the polyalkenoic acid to react with each other in the presence of water, and dehydrating and drying the resulting product. The mixing ratio of the fluorine-containing glass to the polyalkenoic acid may be arranged as earlier described. The mixing ratio of water/(fluorine-containing glass and polyalkenoic acid) is 0.1 to 10, preferably 0.2 to 1.5. The resulting material is first roughly ground to such a size as will afford ease of handling, and then ground to a desired particle size.

The second method is a powder dispersion method. This method comprises pulverizing the fluorine-containing glass to a suitable particle size, and dispersing the same into the polyalkenoic acid in the presence of excess water. The particle size of the glass is preferably 0.1 to 10 $\mu$m. The ratio of the fluorine-containing glass to the polyalkenoic acid may be arranged as earlier stated. To facilitate dispersion of the fluorine-containing glass into the polyalkenoic acid, it is preferable to arrange for presence of excess water. The mixing ratio of water/(fluorine-containing glass and polyalkenoic acid) is 1 to 10, preferably 1.5 to 7.5. The progress of reaction between the fluorine-containing glass and the acid can be monitored by measuring changes in pH. After the process of reaction is nearly completed, water is removed by means of, for example, a hot air oven. Finally, drying is effected to give a pre-formed glass ionomer filler of the invention. Drying may be carried out by using any known method, e. g., by spray drying and/or freeze drying.

In the event that agglomeration should occur, further pulverization may be needed. In case that there remain unreacted glass, the above described process may be repeated.

The third method is a simultaneous reaction and pulverization method which comprises pulverizing a melt of fluorine-containing glass in the presence of polyalkenoic acid and excess water while allowing a reaction to be effected in the mean time. For this purpose, balls, rods, beads, and a planetary or oscillating mill may be used. Any wet milling process may be employed. In this third method, glass agglomerates or melts of from 3 mm to 20 mm in bulk size are pulverized by means of a suitable mill in conjunction with polyalkenoic acid and excess water. The acid matter reacts with the surface of the glass material and, as cement is formed on the surface, destruction occurs to allow appearance of a new glass surface. Conceivably, such surfaces successively go into reaction with acid, with the result that a dispersion liquid of fine particles is obtained. The mixing ratio of the fluorine-containing glass to the polyalkenoic acid is arranged as earlier described. The mixing ratio of water/(fluorine-containing glass and polyalkenoic acid) is 1.0 to 10, preferably 1.5 to 7.5. After the process of reaction is nearly completed, water is removed and the filler is subjected to spray drying and/or freeze drying, whereby a pre-formed glass ionomer filler of the invention is obtained.

The obtained pre-formed glass ionomer filler may be subjected to surface treatment. Useful surface treating agents include, for example, silane compounds, such as vinyltriethoxysilane, vinyltrimethoxysilane, vinyltrichlorosilane, vinyl ($\beta$-methoxy-ethoxy) silane, $\gamma$-methacryloxypropyl trimethoxysilane, $\gamma$-glycidoxypropyl trimethoxysilane, $\gamma$-mercaptopropyl trimethoxysilane, and $\gamma$-aminopropyl triethoxysilane; and titanium compounds, such as isopropyltriisostearoyl titanate, isopropyltridecyl benzene sulfotitanate, tetraoctyl di(tridecylphosphite) titanate, dicumylphonolate oxyacetate titanate, and diisostearoyl ethylene titanate. Preferably, surface treatment is effected with a silane coupling agent, and more particularly, with $\gamma$-methacryloxypropyl trimethoxysilane. By carrying out a surface treatment it is possible to provide some reinforcing effect where mixing with resins is to be made.

Primarily, a silane coupling treatment involves heat treatment at a temperature of more than 100° C. However, since pre-formed glass ionomer fillers of the invention are comparatively vulnerable to heat, it is necessary that heat treatment be carried out at a temperature of not more than 100° C. in an inert gas atmosphere, and that drying be carried out under reduced pressure or vacuum.

The fluoride-ion sustained release pre-formed glass ionomer filler of the invention can provide stable fluoride-ion release for a long time. Even a filler which has once been caused to release fluoride ions may be again dispersed in water after having been dried. In that case, it is possible to obtain a fluorine ion concentration of substantially same value as previously obtained. Only a short time is required for fluoride ion release. In use, the filler may be dispersed in water and there can be instantly recognized a fluoride ion release. Even after that, the filler can long provide stable fluoride ion release.

The pre-formed glass ionomer filler of the invention is able to release a relatively large amount of fluoride ions in the presence of water for a long time. While a fluoride ion release may occur due to hydrolysis of a compound, such release occurs mainly through a ligand exchange that involves no compound dissociation. Therefore, any fluoride ion release by the filler involves little or no possibility that as in conventional dental compositions, any compound used therein, such as sodium fluoride, aluminum fluoride, or sodium monofluorophosphate, is dissolved in water, which in effect results in a disintegration of the compound itself.

When a pre-formed glass ionomer filler of the invention was dispersed in water, fluoride ion concentrations of the following order were obtained.

| filler | Ion-exchanged water | Fluoride ion concentration |
|---|---|---|
| 2 g | 50 g | 39.2 ppm |
| 0.2 g | 50 g | 13.1 ppm |
| 0.02 g | 50 g | 3.11 ppm |
| 0.002 g | 50 g | 0.6 ppm |
| 0.0002 g | 50 g | 0.2 ppm |

As may be seen from the above tabulation, a decrease to 1/10 in the quantity of filler does not mean that the fluoride ion concentration is reduced to 1/10, but the fluoride ion concentration is in an equilibrium state such that the fluoride ion supply is replenished as it is consumed from the water.

The fluoride-ion sustained release pre-formed glass ionomer filler of the invention has a characteristic feature that it will release fluoride ion sustainedly without involving any compound disintegration. Therefore, the filler can be advantageously incorporated into dental compositions which require fluoride ion release, in response to various application needs in dentistry.

For example, the filler can be used in the following applications: dental cement, dental composite resins, bonding agent, treating agent for teeth, primer for teeth treatment, bonding primer, dental adhesive resin cement, fissure sealant, orthodontics adhesive, tooth and root surface coatings, dental material for core build-up, dental lining material, temporary sealing material, root canal filling agent, capping agent, dentifrice, and mouth rinsing agent.

In particular, where the pre-formed glass ionomer filler of the invention is loaded in a dental composition, such as dental cement, which is required to be cured within an oral cavity, it is not necessary to depend for curing upon a glass/ionomer reaction, which results in increased selectable varieties of available resin compositions, cements, etc.

Therefore, the present invention further presents dental compositions comprising a fluoride-ion sustained release pre-formed glass ionomer filler.

As typical dental composition there is provided a dental composition which comprises, in combination with the fluoride-ion sustained release pre-formed glass ionomer filler, a resin composition comprised of (a) radical polymerizable compound and (b) a curing agent.

The resin is preferably chosen to satisfy the following requirements: it should give a final composition that has a suitable viscosity and is not tacky since excess tack will result in the composition sticking to dental instruments; it should act as a binder for the filler and provide a polymerisable matrix in the final composite which is strong and stable in the oral environment; and it should be compatible with the filler in order that a stable dispersion may be formed that does not settle or separate on standing.

Since the pre-formed glass ionomer filler of the present invention is hydrophilic, the resin should be hydrophilic. Alternatively a surfactant or dispersing aid can be used to stabilize the dispersion. The use of a hydrophilic resin has the added benefit that it facilitates the fluoride release from the filler by allowing hydroxyl groups from the saliva to exchange with the fluoride in the filler.

Ideally, the resin should have adhesive properties to dental tissues that are comparable to those of known cements and which are preferably via pendant carboxyl groups along the backbone. This adhesion can be increased by substituting backbone carboxyl groups with phosphate, phosphonate or amino groups. These increase the hydrophilic character of the resin.

The radical polymerizable compound used in a dental composition of the invention is selected from among compounds containing unsaturated double bond groups which are highly safe relative to living organisms and which are widely used in dentistry and chemical industry fields. In particular, monomers, oligomers, and polymers which have more than one unsaturated double bond group, such as (meth)acryloyl group, (meth)acrylamide group, or vinyl group.

The term "(meth)acrylates" used herein means both acrylates and methacrylates.

Specifically, compounds having, in addition to an unsaturated double bond group, any of groups such as phenyl group, hydroxyl group, acid group, acid amide group, amino group, thiol group, disulfide group, cyclic group, heterocyclic group, halogen group, silanol group, pyrrolidone group, urethane bond, ester bond, ether bond, and alkylene glycol group, in more than one in number or in plurality, are mentioned as such by way of example. Especially preferred radical polymerizable compounds are (meth)acrylate ester derivatives having such functional group and/or bond.

It will therefore be appreciated that the resin will normally be made up of more than one polymerisable species in order to satisfy the broad range of requirements. Typically, the resin will comprise 10 to 70 weight percent, preferably 13 to 50 weight percent, more preferably 15 to 40 weight percent of diluents/viscosity reducers; 10 to 89.8 weight percent, preferably 15 to 70 weight percent, more preferably 20 to 70 weight percent of strength inducing copolymers/oligomers; 0 to 50 weight percent, preferably 1 to 30 weight percent, more preferably 3 to 10 weight percent of hydrophilic structure including hydrophilic adhesives; and 0.1 to 50 weight percent, preferably 0.3 to 40 weight percent, more preferably 0.5 to 20 weight percent of adhesion promoters.

Suitable diluents/viscosity reducers include mono-, di-, tri-, or tetra-, ethyleneglycoldi(meth)acrylates, polyethyleneglycol(meth)acrylates, 1,4-di{(meth)acryloxy}butylene, 1,6-di{(meth)acryloxy}hexamethylene, neopentylglycoldi(meth)acrylate, tetramethylolpropanetetra(meth)acrylate, methyl(meth)acrylate, (meth)acrylamide and stylene.

Ethyleneglycoldi(meth)acrylate and triethyleneglycoldi(meth)acrylate are particularly suitable. Two or more of these compounds can be used together, if desired.

If the amount of the above-described diluents/viscosity reducers in the resin is less than 10% by weight or greater than 70% by weight, the mechanical and adhesive properties may be adversely affected.

Suitable strength inducing copolymers/oligomers include urethane(meth)acrylates, including urethane di-, tri-, and tetra-(meth)acrylates.

"Urethane di-(meth)acrylate" means the reaction product of suitable diisocyanates and hydroxyalkyl-mono-(meth)acrylates in 1:2 molar ratio. "Urethane tri-(meth)acrylate" means the reaction product of suitable diisocyanates and hydroxyalkyl-di-(meth)acrylates and hydroxyalkyl-mono-(meth)acrylates in 1:1:1 molar ratio. Urethane tetra-(meth)acrylate means the reaction product of suitable diisocyanates and hydroxyalkyl-di-(meth) acrylates in 1:2 molar ratio.

Particular examples of these kinds of compounds are:
di-{(meth)acryloxyethyl}trimethylhexamethylene diurethane;

di-{(meth)acryloxypropyl}trimethylhexamethylene diurethane;
di-{(meth)acryloxybutyl}trimethylhexamethylene diurethane;
di-{(meth)acryloxypentyl}trimethylhexamethylene diurethane;
di-{(meth)acryloxyhexyl}trimethylhexamethylene diurethane;
di-{(meth)acryloxydecyl}trimethylhexamethylene diurethane;
di-{(meth)acryloxyethyl}isophorone diurethane;
di-{(meth)acryloxypropyl}isophorone diurethane;
di-{(meth)acryloxybutyl}isophorone diurethane;
di-{(meth)acryloxypentyl}isophorone diurethane;
di-{(meth)acryloxyhexyl}isophorone diurethane;
di-{(meth)acryloxyethyl}hexamethylene diurethane;
di-{(meth)acryloxyethyl}tolylene diurethane; the reaction product of 1,1,3-trimethylhexamethylenediisocyante and 2-hydroxypropyl-di-(meth)acrylate in 1:2 molar ratio;
the reaction product of isophoronediisocyanate and 2-hydroxypropyl-di-(meth)acrylate in 1:2 molar ratio;
the reaction product of tolylrenediisocyanate and 2-hydroxypropyl-di-(meth)acrylate in 1:2 molar ratio;
the reaction product of 1,1,3-trimethylhexamethylenediisocyanate and 2-hydroxyethyl(meth)acrylate and 2-hydroxypropyl-di-(meth)acrylate in 1:1:1 molar ratio;
and the reaction product of isophoronediisocyanate and 2-hydroxyethyl(meth)acrylate and 2-hydroxypropyl (meth) acrylate in 1:1:1 molar ratio.

Di-{(meth)acryloxyethyl}trimethylhexamethylene diurethane, di-{(meth)acryloxypentyl}trimethylhexamethylene diurethane, di-{(meth)acryloxyhexyl}trimethylhexamethylene diurethane, di-{(meth)acryloxyethyl}isophorone diurethane, di-{(meth)acryloxypentyl}isophorone diurethane and di-{(meth)acryloxyhexyl}isophorone diurethane are particularly suitable. Two or more kinds of these compounds can be used together if desired.

Other examples of suitable strength inducing copolymers/oligomers include 2,2-bis[4-(2-hydroxy-3-methacryloyloxpropoxy)phenyl]propane, 2,2,bis[4(2-methacryloyloxyphenyl]propane, 2,2-bis[4(3-methacryloyloxypropoxy)phenyl]propane, bis(acryloyloxymethyl)tricyclo(5.2.1.0$^{2,6}$)decane, and diurethane dimethacrylate.

If the amount of strength inducing copolymers/oligomers in the resin is less than 10% or more than 90% by weight, the physical properties may deteriorate.

Examples of suitable hydrophilic structures are polymerisable monomers having hydroxy groups or pyrrolidone groups.

Particular examples include 2-hydroxyethyl(meth)acrylate, 2- or 3-hydroxypropyl(meth)acrylate, 4-hydroxybutyl(meth)acrylate, 5-hydroxypentyl(meth)acrylate, 6-hydroxyhexyl(meth)acrylate, 10-hydroxydecyl(meth)acrylate, diethyleneglycol-mono(meth)acrylate, triethyleneglycol-mono(meth)acrylate, tetraethyleneglycol-mono(meth)acrylate, polyethyleneglycol-mono(meth)acrylate, dipropyleneglycol-mono(meth)acrylate, polypropyleneglycol-mono(meth)acrylate, 1,2- or 1,3- or 2,3-dihydroxypropyl(meth)acrylate, 2-hydroxypropyl-1,3-di(meth)acrylate, 3-hydroxypropyl-1,2-di(meth)acrylate, 2,3,4-trihydroxybutyl(meth)acrylate, N-(2-hydroxyethyl)(meth)acrylamide, N-(2,3-dihydroxypropyl)(meth)acrylamide, N-(meth)acryloyl-1,3-dihydroxypropylamine, vinylpyrollidone and addition products of phenols with glycidyl(meth)acrylate such as 1-phenoxy-2-hydroxypropyl(meth)acrylate, 2-hydroxy-3-naphthoxypropyl(meth)acrylate and an adduct of bisphenol-A and glycidyl(meth)acrylate, and 2-hydroxyethyl(meth)acrylate.

2,3-dihydroxypropyl(meth)acrylate, N-(2-hydroxyethyl)(meth)acrylamide, N-(2,3-dihydroxypropyl)(meth)acrylate and vinyl pyrrolidone are particularly suitable. Two or more of these compounds may be used together.

Suitable hydrophilic adhesives include 4-acryloxyethyltrimeric acid, 4-methacryloxyethyl-trimellitate anhydride, the phosphate esters described in EP 237233, EP 334934, EP 155312, EP 055453, GB 2172889, US 4579382, U.S. Pat. No. 4,537,940, U.S. Pat. No. 4,514,342, U.S. Pat. No. 4,515,930, U.S. Pat. No. 4,544,467, U.S. Pat. No. 3,882,600, U.S. Pat. No. 4,499,251, U.S. Pat. No. 4,383,052, U.S. Pat. No. 4,368,043, U.S. Pat. No. 4,259,117, U.S. Pat. No. 4,259,075, U.S. Pat. No. 4,222,780, U.S. Pat. No. 4,182,035, U.S. Pat. No. 4,039,722, U.S. Pat. No. 3,984,500, U.S. Pat. No. 3,957,918 and those having the following structures:

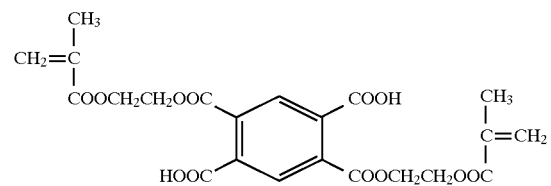

PMDM reaction product of pyromellitic acid anhydride and 2-hydroxyethyl methacrylate in 1:2 molar ratio

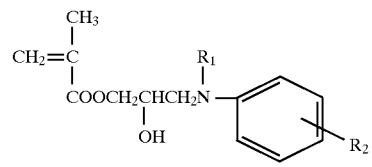

$R_1$ = H   $R_2$ = $CH_3$         (o, m, p)

= n-$C_4H_9$            (p)

= $OCH_3$              (o, m, p)

= COOH                 (o, m, p)

= $COOC_2H_5$          (o, m, p)

= F                    (p)

= Cl                   (p)

= $CH_2COOH$           (p)

$R_1$ = $CH_3$   $R_2$ = COOH      (o, m, p)

reaction product of an aryl amine derivative and glycidylmethacrylate in 1:1 molar ratio, and derivatives their of

NPG-GMA
N-phenyl glycine-glycidylmethacrylate

NTG-GMA
N-toluilglycine-glycidylmethacrylate 1-methacryloyl-4-carboxymethyl piperazine phenylene diamine-N-methacryloyl-N,N'-diacetic acid methacryloxyethyl phtalate p-vinyl benzoicacid N-methacryloyl-6-amino-n-caproic acid R = H : HPPM
CH$_3$ : CH$_3$HPPM
C$_4$H$_9$ : t-BuHPPM
Cl : ClHPPM
O : Phenoxy HPPM
CH$_3$O : CH$_3$OHPPM reaction product of a phenol derivative and glycidylmethacrylate in 1:1 molar ratio, and derivatives their of

HNPM
naphthol-glycidylmethacrylate

N-methacryloyl phenylalanine

N, O-dimethacryloyl tyrosine

R = —O—CH$_2$CH$_2$Br : (Bromo-P)

—O—⌬ : (Phenyl-P)

derivatives of (2-methacryloxyethyl)phosphoric acid p-vinylbenzyl phosphonic acid vinyl phosphonic acid If the amount of the above described compounds in the resin is more than 50% by weight, the mechanical properties may deteriorate.

Suitable adhesion promoters include monomers, oligomers or polymers having polymerisable unsaturated groups such as acryloyl, methacryloyl, vinyl and allyl groups together with acidic groups such as carboxyl groups, phosphoric groups, acid anhydride residues, siloxane groups, acid amide groups, monomers being particularly preferred.

Examples of polymerisable monomers having acidic groups include mono-, di-, tri- or tetra-carboxylic acids and their derivatives such as (meth)acrylic acid, 4-(meth)acryloxyethyltrimellitic acid, 4-(meth)acryloxybutyltrimellitic acid, 4-(meth)acryloxypentyltrimeritic acid, 4-(meth)acryloxyhexyltrimellitic acid, 4-(meth)acryloxydecyltrimellitic acid, 6-(meth)acryloxyethylnaphthalene-1,2,6,-tricarboxylic acid, N,O-di(meth)acryloxytyrosine, N-(meth)acryloxytyrosine, N-(meth)acryloxyphenylalanine, N-(meth)acryloyl-p-aminobenzoic acid, N-(meth)acryloyl-5-aminosalicylic acid, N-(meth)acryloyl-4-aminosalicylic acid, 4-(meth)acryloyl-4-aminosalicylic acid, 4-(meth)acryloyloxybenzoic acid, p-vinylbenzoic acid, o-(meth)acryloxytyrosineamide, -phenylglycine-glycidyl(meth)acrylate, -toluilglycine-glycidil(meth)acrylate, the reaction product of pyromellitic acid and 2-hydroxyethyl(meth)acrylate in 1:2 molar ratio, 11 (meth) acryloxy-1,1-undecanedicarboxylic acid, bis-{2-(meth)acryloxyethyl}phosphoric acid, {2-(meth)acryloxyethylphenyl}phosphoric acid, 10-(meth)acryloxydecyldihydrogen phosphate, vinylphosphoric acid, p-vinylbenzylphosphoric acid, 4-(meth)acryloxyethyltrimellitic acid anhydride, 4-(meth)acryloxyhexyltrimellitic acid anhydride, N-(meth)acryloxyethyltyrosineamide and gamma-methacryloxyethyltrimethoxy silane. 4-(meth)acryloxyethyltrimellitic acid, 4-(meth)acryloxyethyltrimellitic acid anhydride, 4-(meth)acryloxyhexyltrimellitic acid, 4-(meth)acryloxyhexyltrimellitic acid anhydride, N-phenylglicine-glycidil(meth)acrylate, N-toluilglycine-glycidil(meth)acrylate, an adduct of pyromellitic acid anhydride and 2-hydroxyethyl(meth)acrylate in 1:2 molar ratio, 11-(meth)acryloxy-1,1-undecane dicarboxylic acid, {2-(meth)acryloxyethylphenyl}phosphoric acid, 10-(meth)acryloxydecyldihydrogen phosphates p-vinylbenzylbenzylphosphonic acid and gamma-methacryloxyethyltrimethoxy silane are particularly suitable among them. Two or more kinds of these compounds may be used together.

In case when the amount of the adhesion promoters in the resin is less than 1% by weight or more than 50% by weight, the adhesive properties may deteriorate.

The curing agent used in a dental composition of the invention may be selected from among those initiators and accelerators which are widely used as catalysts for radical polymerization in such fields as dentistry and chemical industry. With a curing agent so selected, the dental composition of the invention may be cured through photopolymerization, chemical polymerization or through both photopolymerization and chemical polymerization (dual cure).

An initiator for radical polymerization is selected from among organic peroxides for chemical polymerization, and sensitizers for ultraviolet light or visible light polymerization, such as benzoin derivative, α-diketones, and trialkylborons. More than one may be selected from among these initiators so as to suit the radical polymerizable compound and the desired curing method.

Specifically, useful organic peroxides include, for example, benzoyl peroxide, 4,4'-dichloro benzoyl peroxide, dicumyl peroxide, tert-butylperbenzoate, tert-butylperoxymaleic acid. Especially preferred are benzoyl peroxide, tert-butylperbenzoate, and tert-butyl peroxymaleic acid.

Examples of sensitizers for ultraviolet light and visible light are benzoin, benzoin methylether, benzoin ethylether, benzoin isopropylether, 5 benzophenone, 9,10-anthraquinone, 2-hydroxy-3-(3,4-dimethyl-9H-thioxanthine-2-yloxy)-N,N,N-trimethyl-1-propane ammonium chloride, camphorquinone, benzyl, 4,4'-dichlorobenzyl, and diacetyl, which are preferred for use as initiating agents for photopolymerization.

An accelerator for radical polymerization may be selected from among amine, barbituric acid derivatives, organic tin compounds, and alkali metal or alkali earth metal salt, or amide salt of sulfinic acid, according to the mode of curing to be employed.

Preferred polymerization accelerators are N-methyldiethanolamine, tributyl phosphine, allyl thiourea, and N,N-dimethyl-p-toluidine. Suitable accelerators for photopolymerization to be used in this invention include organic nitrogen compounds such as amine and barbiturates or organic tin-compounds.

Particular examples of these accelerators for photopolymerization include N,N-dimethyl-p-toluidine, N,N-(2-hydroxyethyl)-p-toluidine, triethylamine, N-methylethanolamine, N,N-dimethylaminoethyl methacrylate, N,N-diethylaminoethylmethacrylate, N-phenylglycine-glycidoylmethacrylate, barbituric acid, 1,3-dimethylbarbituric acid, 1-methylbarbituric acid, 1,3-diphenylbarbituric acid, 5-butylbarbituric acid, 1,5-dimethylbarbituric acid, 5-ethylbarbituric acid, 5-isopropylbarbituric acid, 5-cyclohexylbarbituric acid, 1,3-dimethyl-5-ethylbarbituric acid, 1,3-dimethyl-5-n-butylbarbituric acid, 1,3-dimethyl-5-isobutylbarbituric acid, 1,3-dimethyl-5-cyclohpentylbarbituric acid, 1,3-dimethyl-5-cyclohexylbarbituric acid, 1,3,5-dimethyl barbituric acid, 1,3-dimethyl-5-phenylbarbituric acid, 1-benzyl-5-phenylbarbituric acid, icyclohexyl-5-ethyl barbituric acid, thiobarbituric acid, 1,3,5-trimethyl-2-thiobarbituric acid, 5-butyl-2-thiobarbituric acid, salts of these barbituric acid derivatives (particularly salts of alkali metals or alkaline earth metals), di-n-butyl-tin-maleate, di-n-butyl-tin-maleate (polymer); di-n-octyl-tin-maleate, di-n-octyl-tin-maleate (copolymer), di-n-octyl-tin-dilaurate and di-n-butyl-tin-dilaurate.

For the alkaline metal or alkaline earth metal or amide salts of sulfinic acid, aromatic sulfinic acids or salts thereof are advantageously used. Preferably, benzene sulfinic acid, sodium benzenesulfinate, alkyl group-substituted sodium benzenesulfinate, and p-toluene sodium sulfinate, which are conventionally used in dentistry, are exemplified as such. Examples of aromatic sulfinyl amides are N,N-dimethyl-p-toluenesulfinyl amide, benzene sulfinyl amide, N,N-dimethyl-p-toluenesulfinyl amide, benzene sulfinyl amide, N,N-dimethyl-p-toluenesulfinic acid morpholide, and p-toluenesulfinic acid morpholide.

Accelerator/initiator combinations for radical polymerization which are used as curing agents in the case of chemical reaction at room temperature in the present invention include, for example, tri-n-butyl borane, aromatic tertiary amine/benzoyl peroxide, aromatic sulfinic acid or salt thereof/aromatic tertiary amine/diacyl peroxide, barbituric acid derivative/aromatic tertiary amine/diacyl peroxide, barbituric acid derivative/copper ion/halogen compound, aromatic sulfinic acid or salt thereof/aromatic tertiary amine/t-butylperoxymaleic acid, aromatic sulfinyl amide/aromatic tertiary amine/t-butylperoxymaleic acid, which are all advantageously used. Also, a combination of cobalt naphthenate/methylethyl peroxide may be exemplified as such.

For the purpose of curing in the case of photopolymerization, particularly preferred initiators and accelerators for photopolymerization include camphor quinone, benzyl, diacetyl, N,N-di-methylaminoethyl methacrylate, N,N-diethylaminoethyl methacrylate, 1,3,5-trimethylbarbituric acid, 5-butylbarbituric acid, 1-benzyl-5-phenylbarbituric acid, 1,3-dimethyl-5-isobutylbarbituric acid, 1-cyclohexyl-5-ethylbarbituric acid, 1,3,5-trimethyl-2-thiobarbituric acid, and di-n-butyl-tin-dilaurate. When desired, two or more of the foregoing initiators and accelerators for photopolymerization may be used together.

Where curing is to be carried out by both photopolymerization and chemical polymerization, that is, dual curing is to be made, two or more may be selected from among the foregoing chemical and photo polymerization catalysts as required.

Also suitable is the catalyst described in GB 1,408,265 which comprises (a) at least photosensitizer having the structure

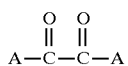

where the groups of A, which may be the same or different, are hydrocarbyl or substituted hydrocarbyl groups, and in which the groups A may be further linked together by a direct link or by a divalent hydrocarbyl group, or in which the groups A together may form a fused aromatic ring system; and (b) at least one reducing agent capable of reducing the photosensitizer when the photosensitizer is in an excited state and having the structure

where the units R, which may be the same or different, are hydrogen atoms, hydrocarbyl groups, substituted hydrocarbyl groups or groups in which two units R together with the nitrogen atom form a cyclic ring system, no more than two of the units R being hydrogen atoms or substituted hydrocarbyl groups and, where the nitrogen atom is attached directly to an aromatic group R, at least one of the other units R has a —C(H)— group attached to the nitrogen atom.

The catalysts described in GB 2218104 are also suitable, in particularly di-butyl tin dilaurate with camphoroquinone; and catalysts of the following structures:

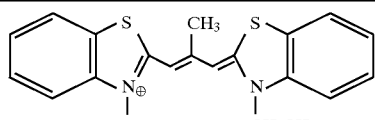
Ph$_3$B$^\ominus$n-C$_4$H$_9$

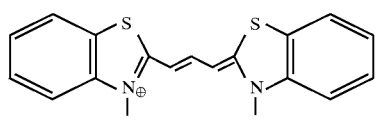
Ph$_3$B$^\ominus$n-C$_4$H$_9$

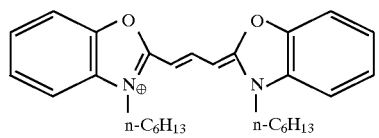
Ph$_3$B$^\ominus$n-C$_4$H$_9$

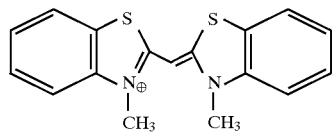
Ph$_3$B$^\ominus$n-C$_4$H$_9$

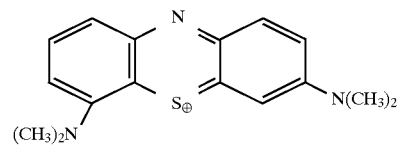
Ph$_3$B$^\ominus$n-C$_4$H$_9$

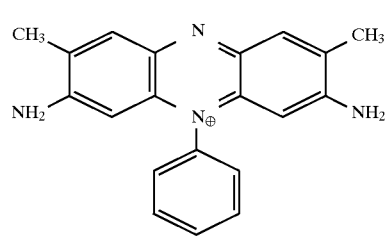
Ph$_3$B$^\ominus$n-C$_4$H$_9$

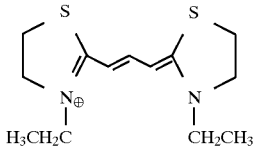
Ar$_3$B$^\ominus$—R'

| R' | Ar |
|---|---|
| n-butyl | phenyl |
| n-hexyl | phenyl |
| n-butyl | anisyl |

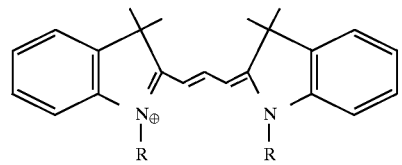
Ar$_3$B$^\ominus$—R'

| R' | R | Ar |
|---|---|---|
| methyl | n-butyl | phenyl |
| methyl | n-hexyl | phenyl |
| n-butyl | n-butyl | phenyl |
| n-butyl | n-hexyl | phenyl |
| n-heptyl | n-butyl | phenyl |
| n-heptyl | n-hexyl | phenyl |
| ethyl | n-butyl | phenyl |

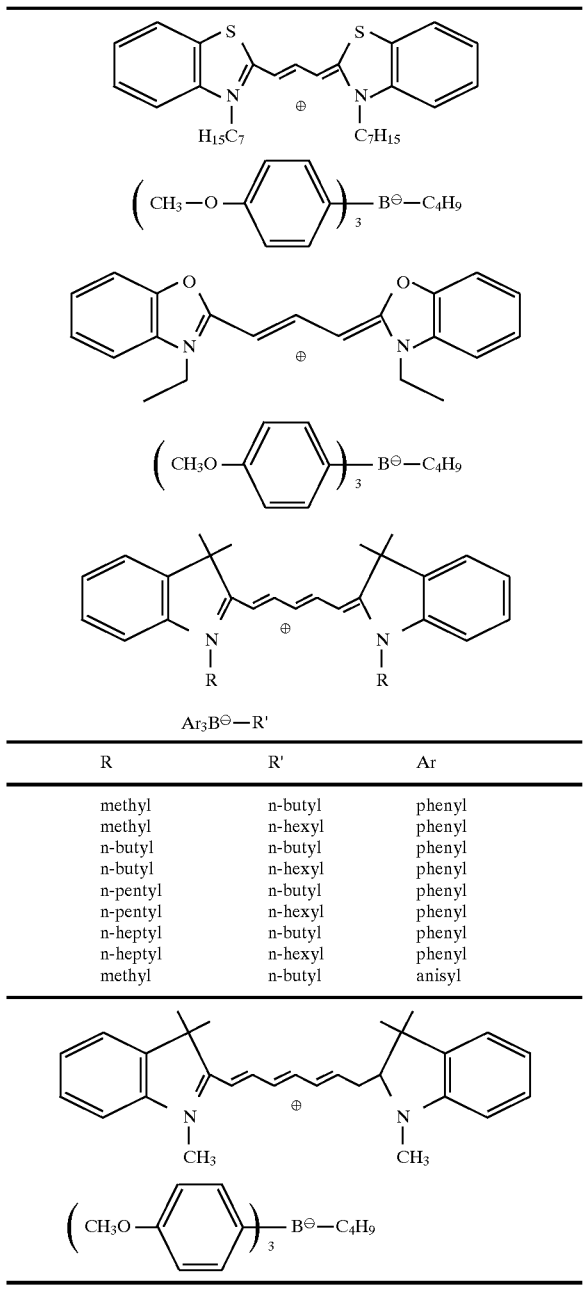

The catalysts described in GB 1,408,265 and GB 2,218, 104 are particularly suitable for use with light in the blue region of the electromagnetic spectrum, i.e. light centered around 470 nm. The remaining catalysts cover a much wider spectrum, including red, orange, yellow and green light.

If the catalyst is used in an amount of less than 0.1 weight percent or more than 15 weight percent, there may be a deterioration in adhesive properties.

Where the proportion of the curing agent is less than 0.1 wt % or more than 15 wt % relative to the resin composition, such proportion is undesirable, because the adhesion performance may be adversely affected.

In the present invention, the proportion of the pre-formed glass ionomer filler relative to a dental composition is 1 to 90 wt %, preferably 5 to 80 wt %. If the pre-formed glass ionomer filler content is less than 1 wt %, any satisfactory fluoride ion release performance cannot be obtained, and if the filler content is more than 90 wt %, the composition, when used in tooth treatment, does not provide any sufficient post-cure strength. Therefore, any such relative insufficiency or excess is undesirable.

The dental composition of the invention may have, in addition to the pre-formed glass ionomer filler, other inorganic filler, organic composite filler, organic polymer, etc. incorporated therein, in order to provide various characteristic features necessary for dental purposes.

Useful inorganic fillers include all known fillers and, in particular, ultrafine colloidal silica, quartz, silica, kaolin, talc, barium glass, strontium glass, alumina, aluminosilicate, silicon nitride, barium sulfate, calcium silicate, calcium phosphate, and glass powder, which are all advantageously used.

Suitable organic composite fillers include, for example, organic fillers obtained as by grinding a hardened thermosetting resin material or a hardened thermosetting resin material containing an inorganic filler, composite fillers comprising an inorganic filler and an organic filler, and fillers obtained by grinding a hardened mixture of, for example, micro-particle colloidal silica and resin.

Useful organic polymers include, for example, polystyrene, polymethyl methacrylate, polyethyl methacrylate, and a copolymer of polymethyl methacrylate and polyethyl methacrylate.

The dental composition of the present invention may further contain a shelf-life stabilizer. Preferred shelf-life stabilizers include, for example, hydroquinone, hydroquinone monomethylether, and butylated hydroxytoluene.

Further, the dental composition of the invention may have water and/or organic solvent contained therein. Particularly useful for this purpose are, for example, water, methyl alcohol, ethyl alcohol, ethyl acetate, chloroform, methyl ethyl ketone, acetone, benzene, toluene, and xylene. Of these, water, ethyl alcohol, and acetone are particularly preferred.

Where the curing agent is a light cure catalyst from among initiator/accelerator combinations for photopolymerization, and where resin curing is effected only through photopolymerization reaction, it is preferable to premix the radical polymerizable compound and the light cure catalyst together and disperse the pre-formed glass ionomer filler in the mixture. The fluorine-containing glass and the polyalkenoic acid have already reacted with each other, and there is no need for any further cure reaction with respect to them. Therefore, the process of curing the dental composition is controlled only by curing the resin composition. The progress of curing under ordinary daylight is very slow. This enables manufacture of a one pack light-curable cement which in effect will not cure until it is exposed to bright light.

The present invention provides a paste-form one pack light-curable cement comprising a photopolymerizable resin composition and a fluoride-ion sustained release pre-formed glass ionomer filler dispersed therein, which need not be manually or mechanically mixed prior to use. The one pack light-curable dental cement does not cure under ordinary daylight, but will become fast cured within an oral cavity when it is exposed to light illumination after being applied for tooth treatment. This eliminates problems with prior art cement, such as nonuniformity of mixing, air bubble inclusion into post-cure cement, delay in curing, and curing while in storage. Another advantage of this dental cement is that the cement exhibits much more satisfactory fluoride-ion releasing performance than conventional glass ionomer for a long time.

For the purpose of being compounded into the one pack light-curable dental cement of the invention, the pre-formed glass ionomer filler may have a particle size of 0.01 to 100 μm, preferably 0.1 to 10 μm. The mixing ratio of a resin composition to the pre-formed glass ionomer filler is preferably from 20:80 to 70:30 in volume ratio.

In this case, other inorganic filler, organic composite filler, and/or organic polymer may be added in addition to the pre-formed glass ionomer filler of the invention, which still provides for such satisfactory fluoride-ion release as is well consistent with the objective of the invention.

The one pack light-curable dental cement of the invention may contain any compound other than the pre-formed glass ionomer filler which can release fluoride ions. For example, hydrolyzable fluorides, such as sodium fluoride, aluminum fluoride, potassium fluoride, and sodium monofluorophosphate, are advantageously used. In order to facilitate liberation of such fluoride ion from the cement, the resin composition is preferably so arranged as to contain a hydrophilic resin composition.

To manufacture the one pack light-curable dental cement, a radical polymerizable compound and a light cure catalyst are premixed and the pre-formed glass ionomer filler is dispersed in the mixture.

The pre-formed glass ionomer filler of the invention is produced by glass ionomer reaction and has a function to release fluoride ion sustainedly by itself without involving disintegration of a compound. The filler may be compounded into known cements, such as zinc phosphate cement, carboxylate cement, and glass ionomer cement, which have conventionally been used in the art of dentistry, in order to improve the handling and performance characteristics of the prior art cements.

The invention provides a dental composition which contains a fluoride-ion sustained release pre-formed filler and, in addition thereto, (A) a dental inorganic cement powder material and (B) a dental cement liquid material.

For the dental inorganic cement powder material, any known powder material of the type may be used. For example, zinc oxide, glass material for glass ionomer cement, and mixtures thereof may be mentioned as such.

For the dental inorganic cement liquid material, any known material of the type may be suitably used. For example, phosphoric acid, eugenol, ethoxybenzoic acid, and homopolymer or copolymer of polyalkenoic acid may be enumerated as such.

In dental inorganic cements and, more particularly, glass ionomer cements, for the powder material and liquid material, aforesaid fluorine-containing glasses and polyalkenoic acids may be used as they are in the production of the pre-formed glass ionomer filler of the invention.

For the purpose of regulating cement cure reaction, any known regulator may be used. Specifically, chelating agents, such as tartaric acid and citric acid, phosphoric acid, and zinc acetate may be exemplified as such. Further, the composition may contain additives, such as X-ray opaque material, tannic acid and derivative thereof, and pigment.

When the pre-formed glass ionomer filler of the invention is to be loaded into a dental inorganic cement, the proportion of the filler may be determined according to the type of the cement composition.

Typically, the proportion is from 1 to 90 wt %, preferably from 5 to 70 wt %, especially preferably from 8 to 40 wt %. If the proportion is less than 1 wt %, any satisfactory fluoride ion release performance cannot be achieved. If the proportion is more than 90 wt %, the curing performance of the cement is reduced.

The dental composition of the invention may comprise, in addition to the filler-containing cements, a resin composition loaded therein which is comprised of a radical polymerizable compound and a curing agent. For the resin composition, those exemplified above are all preferably used. Further, polyalkenoic acids having an unsaturated group in a side chain are useful which have hitherto been disclosed in the art of dentistry.

When such resin composition is to be loaded, in addition to an inorganic cement, into a dental composition, the dental composition is cured by photopolymerization and/or chemical polymerization, in addition to an inherent cement cure reaction.

Because of its quick fluoride-ion release performance in the presence of water, the fluoride-ion sustained release pre-formed glass ionomer filler of the invention may be loaded into dental compositions, such as tooth paste, toothwash, and rinsing agent, which are intended to produce fluorine-aided tooth strengthening, dental-caries preventing, and hypersensitivity restraining effects.

A dental composition of the invention may comprise, in addition to the pre-formed glass ionomer filler, any suitable ingredient as desired according to the type of the composition. The composition may be prepared in accordance with a conventional method. For example, where preparation of a tooth paste is intended, various effective ingredients, such as abrasive material, lubricant, surface active agent, sweetener, and preservative, may be compounded together in such a way that the ingredients, together with water, are mixed and kneaded into paste. Specifically, abrasive materials available for use include, for example, precipitated silica, silica gel, aluminosilicate, and zirconosilicate, which are known as silica-based abrasive materials; and dibasic calcium phosphodihydrate, dibasic calcium phosphoanhydride, calcium pyrophosphate, calcium carbonate, aluminum hydroxide, titanium dioxide, alumina, magnesium carbonate, tribasic magnesium phosphate, and zeolite, which are known as synthetic resin-based abrasive materials. Viscous wetting agents available for use include, for example, glycerine, sorbitol, propylene glycol, and polyethylene glycol; and caking agents available for use include, for example, sodium carboxymethyl cellulose, hydroxyethyl cellulose, carrageenan, sodium alginate, xanthane gum, sodium polyacrylate, polyvinyl alcohol, locust bean gum, Carbopol, guar gum, montmorillonite, and gelatin. Useful surface active agents include, for example, sodium lauryl sulfate, a-sodium olefosulfate, N-acyl sarcosinate, N-acyl glutamate, N-acyl taurate, sucrose aliphate, alkylol amide, polyoxyethylene hardened castor oil and polyglycerin aliphates ester. Sweeteners includes, for example, sodium saccharate, stevioside, paramethoxycinnamic aldehyde, neohesperidyl dihydrochalcone, and pararutin. Useful preservatives include, for example, paraoxybenzoate and sodium benzoate. Useful as other effective ingredients are allantoin chlorohydroxy aluminum, hinokitiol, ascorbic acid, lysozyme chloride, glytyrrhetic acid and salts thereof, sodium chloride, dl-a-tocopherol acetate, α-bisabolol, isopropyl methyl phenol, chlorohexidine salts, cetylpyridinium chloride, azulene, glycyrrhetic acid, sodium copper chlorophyllin, aluminum lactate, berberine, hydroxamic acid and derivatives thereof, dextranase, mutanase, amylase, polyvinyl pyrrolidone, epidihydrocholesterol, benzetonium chloride, dihydrocholesterol, tranexamic acid, trichlorocarbanilide, zinc citrate, Japanese angelica root (ligusticum root) extract, and extracts of clove, rosemary, golden flower, safflower, etc. Also, mention may be made of perfumes, such as 1-menthol, carvonl, and anethole, and pigments, such as Blue No. 1 and Yellow No. 4.

A dental composition of the invention may be packaged in a suitable container, such as aluminum foil laminated tubelike plastic container or plastic bottle-form container. Such composition in powder form may be packaged in a tea bag-like container.

In the case of tooth pastes, the dental composition preferably contains a sufficient amount of the pre-formed glass ionomer filler to provide a within-mouth fluoride ion concentration of 0.0001 to 2%, more particularly 0.001 to 0.2%. Any other fluoride-ion releasing composition may be used in combination with the filler.

As described above, a dental composition of the invention which contains the fluoride-ion releasable pre-formed glass ionomer filler need not always be of the one-paste type. It may be any of those types of dental compositions which are conventionally available as such, including one-paste type, two-paste type, three-paste type, paste/liquid type, powder/liquid type, and one-liquid type.

The present invention can be illustrated by the following examples:

EXAMPLE 1

A glass (G1) was prepared by fusing together 21.0% aluminum oxide, 37.4% silica, 24.8% calcium fluoride, and 17.3% aluminum fluoride. The resultant glass was ground to an average diameter of 5 $\mu$m.

EXAMPLE 6

A glass (G6) was prepared by electro-melting together 18.1% aluminum oxide, 26.3% silica, 20.4% calcium fluoride, 1.8% aluminum fluoride, 5.3% cryolite, 4.3% aluminum phosphate and 23.8% gadolinium oxide. The resultant glass was ground to an average diameter of 2 $\mu$m by jet-mill.

The compositions of Examples 1 to 6 are set out in Table 2.

EXAMPLE 7 to 12

Glasses G7 to G12 were prepared having the compositions indicated in Table 2.

TABLE 2

Prepared formulation of raw material (wt %)
(This formulation is not glass composition and correspond to G1–G12 in Table 1)

| | $Al_2O_3$ | $SiO_2$ | $CaF_2$ | $AlF_3$ | $Na_3AlF_6$ | $AlPO_4$ | $Gd_2O_3$ | $GdF_3$ | $La_2O_3$ | $LaF_3$ | $YbF_3$ | $ZrSiO_4$ | $SrF_2$ |
|---|---|---|---|---|---|---|---|---|---|---|---|---|---|
| G1 | 21.0 | 37.4 | 24.3 | 17.3 | — | — | — | — | — | — | — | — | — |
| G2 | 18.8 | 34.4 | 22.4 | 16.0 | — | 8.4 | — | — | — | — | — | — | — |
| G3 | 18.2 | 37.0 | 17.3 | 9.6 | 5.5 | 12.4 | — | — | — | — | — | — | — |
| G4 | 15.2 | 36.2 | 23.4 | 25.2 | — | — | — | — | — | — | — | — | — |
| G5 | 18.2 | 32.6 | — | 15.2 | — | — | — | — | — | — | — | — | 34.0 |
| G6 | 18.1 | 26.3 | 20.4 | 1.8 | 5.3 | 4.3 | 23.8 | — | — | — | — | — | — |
| G7 | 18.5 | 26.9 | 21.0 | 1.9 | 5.4 | 4.4 | — | — | 21.9 | — | — | — | — |
| G8 | 20.0 | 30.0 | — | — | — | — | — | — | — | 50.0 | — | — | — |
| G9 | 18.4 | 27.3 | — | — | — | — | — | — | — | — | 54.3 | — | — |
| G10 | — | 20.2 | 13.2 | — | — | — | 30.5 | 36.1 | — | — | — | — | — |
| G11 | 19.1 | 31.4 | — | 3.5 | — | — | — | — | — | 32.8 | — | — | 13.2 |
| G12 | 24.8 | 17.5 | 22.8 | 8.2 | — | — | — | — | — | — | — | 26.7 | — |

EXAMPLE 2

A glass (G2) was prepared by fusing together 18.8% aluminum oxide, 34.4% silica, 22.4% calcium fluoride, 8.4% aluminum phosphate and 16.0% aluminum fluoride. The resultant glass was ground to an average diameter of 5 $\mu$m.

EXAMPLE 3

A glass (G3) was prepared by fusing together 18.2% aluminum oxide, 37.0% silica, 17.3% calcium fluoride, 12.4% aluminum phosphate, 9.6% aluminum fluoride and 5.5% cryolite ($Na_3AlF_6$). The resultant glass was ground to an average diameter of 5 $\mu$m.

EXAMPLE 4

A glass (G4) was prepared by fusing together 15.2% aluminum oxide, 36.2% silica, 23.4% calcium fluoride and 25.2% aluminum fluoride. The resultant glass was ground to an average diameter of 3$\mu$m.

EXAMPLE 5

A glass (G5) was prepared by electro-melting together 18.2% aluminum oxide, 32.6% silica, 34.0% strontium fluoride, and 15.2% aluminum fluoride. The resultant glass was ground to an average diameter of 2 $\mu$m.

EXAMPLE 13

Glass synthesis using the sol-gel process
Solex 1: $SiO_2$ 33.6 mol %; $Al_2O_3$ 13.5 mol %; CaO 13.5 mol %; F 39.4 mol %

A 1 l four-necked flask was charged with 61.3 g(0.3 mol) of Al(O-isoPr)$_3$, 62.5 g (0.3 mol) of Si(OEt)$_4$ and 250 ml of benzene. The flask was connected with a thermometer, a condenser, and a teflon stirrer; the mixture was stirred until a clear solution was obtained.

A 100 ml dropping funnel was charged with 35.4 g(0.15 mol) of Ca(NO$_3$)$_2$4H$_2$O, 30.0 g (0.073 mol) of H$_2$SiF$_6$ and 35 ml of demineralized water. When the Ca(NO$_3$)$_2$4H$_2$O had completely dissolved, the dropping funnel was connected to the flask and the solution was added to the flask over a period of one hour at room temperature with continuous stirring. Exothermic change occurred at about 50° C. after 30min.

The reaction mixture was then refluxed at 90° C. for 3 hours with continuous stirring. It was then cooled to room temperature and the wet gel was recovered by decantation. The wet gel was washed twice with 500 ml demineralized water and dried.

The drying process was as follows:
50° C.-12 hours→110° C.-5 hours→150° C.-12 hours

EXAMPLE 14

Procedure of glass synthesis using the sol-gel process
Solex 2: $SiO_2$ 33.6 mol %; $Al_2O_3$ 13.5 mol %; SrO 13.5 mol %; F 39.4 mol %

A 1 l four-necked flask was charged with 112.5 g(0.3 mol) of Al(NO$_6$)9H$_2$O, 62.5 g(0.3 mol) of Si(Oet)$_4$ and 250 ml of EtOH. The flask was connected with a thermometer, a condenser, and a teflon stirrer; the mixture was stirred until a clear solution was obtained A 100 ml dropping funnel was charged with 83.5 g(0.3 mol) of Sr(NO$_3$)$_2$ and 35 ml of demineralized water.

When the Sr(NO$_3$)$_2$ had completely dissolved, the dropping funnel was connected to the flask and the solution was added over a period of one hour at room temperature with continuous stirring. Exothermic change occurred at about 50° C. after 30min.

A 100 ml dropping funnel was charged with 30.0 g(0.073 mol) of H$_2$SiF$_6$ and 35 ml of EtOH and the dropping funnel was attached to the flask and the solution was added to the flask over a period of 0.5 hour room temperature with continuous stirring.

The reaction mixture was then refluxed at 90° C. for 3 hours with continuous stirring. The mixture was cooled to room temperature. The drying process was as follows:

50° C.-24 hours→110° C.-5 hours→450° C.-5 hours

EXAMPLE 15
Glass synthesis using the sol-gel process

Solex 3: SiO$_2$ 28.9 mol %; La$_2$O$_2$ 14.5 mol %; SrO 14.5 mol %; F 42. 2 mol %

A 1 l four-necked flask was charged with 129.9 g(0.3 mol) of La(NO$_3$)$_3$6H$_2$O, 62.5 g(0.3 mol) of Si(OEt)$_4$ and 250 ml of EtOH. The flask was connected with a thermometer, a condenser, and a teflon stirrer; the mixture was stirred until a clear solution was obtained. It was then refluxed for 1.5 hours.

A 100 ml dropping funnel was charged with 31.7 g(0.15 mol) of Sr(NO$_3$)$_2$ and 35 ml of demineralized water.

When the Sr(NO$_3$)$_2$ had completely dissolved, the dropping funnel was connected to the flask and the solution was added to the flask over the period of one hour with continuous stirring. It is then refluxed for 3 hours.

A 100 ml dropping funnel was charged with 18.6 g(0.438 mol) of HF(47%) and 35 ml of EtOH and the dropping funnel was attached to the flask and this solution was added to the flask over a period of 0.5 hour at room temperature with continuous stirring.

The reaction mixture was then refluxed for 3 hours with continuous stirring. The mixture was cooled to room temperature.

The drying process was as follows:

50° C.-24 hours→110° C.-5 hours→450° C.-hours

EXAMPLE 16
Glass synthesis using the sol-gel process

Solex 4: SiO$_2$ 30.8 mol %; Al$_2$O$_3$ 5.8 mol %; Gd$_2$O$_3$ 5.8 mol %; CaO 11.5 mol %; F 46.2 mol %

A 1 l four-necked flask was charged with 56.3 g(0.15 mol) of Al(NO$_3$)$_3$9H$_2$O, 67.7 g(0.15 mol) of Gd(NO$_3$)$_3$6H$_2$O, 62.5 g of Si(OEt)$_4$ and 250 ml of EtOH.

The flask was connected with a thermometer, a condenser, and a teflon stirrer; the mixture was stirred until a clear solution was obtained. It was then refluxed for 1.5 hours. A 100 ml dropping funnel was charged with 35.4 g(0.15 mol) of Ca(NO$_3$)$_2$4H$_2$O and 60 ml of demineralized water.

When the Ca(NO$_3$)$_2$4H$_2$O had completely dissolved, the dropping funnel was connected to the flask and the solution was added to the flask over the period of one hour with continuous stirring. It was then refluxed for 3 hours.

A 100 ml dropping funnel was charged with 18.8 g(0.1 mol) of Na$_2$SiF$_6$ and 60 ml of demineralized water and the dropping funnel was connected to the flask and this solution was added to the flask over a period of 0.5 hour at room temperature with continuous stirring.

The reaction mixture was then refluxed for 3 hours with continuous stirring. The mixture was cooled to room temperature and the wet gel recovered by decantation. The wet gel was washed twice with 500 ml demineralized water and dried. The drying process was as follows:

50° C.-24 hours→110° C.-5 hours→150° C.-12 hours

EXAMPLE 17
Glass synthesis using the sol-gel process

Solex 5: SiO$_2$ 30.0 mol %; Gd$_2$O$_3$ 10.0 mol %; CaO 10.0 mol %; F 50.0 mol %

A 5 l four-necked flask was charged with 225.6 g(0.5 mol) of Gd(NO$_3$)$_3$6H$_2$O 225 g(1.08 mol) of Si(OEt)$_4$ and 3 L of EtOH. The flask was connected with a thermometer, a condenser, and a teflon stirrer; the mixture was stirred until a clear solution is obtained. It was then refluxed for 2 hours.

A 300 ml dropping funnel was charged with 173 g(0.42 mol) of H$_3$SiF$_6$(35 wt % soln.) and 100 ml of EtOH.

When the H$_2$SiF$_6$ has complete uniformity, the dropping funnel was connected to the flask and this solution was added to the flask over two hours with continuous stirring. It was then refluxed for 1 hour.

A 300 ml dropping funnel was charged with 118.1 g(0.5 mol) of Ca(NO$_3$)$_2$4H$_2$O and 200 ml of EtOH and the dropping funnel was connected to the flask and this solution was added over 1 hour at room temperature with continuous stirring.

The reaction mixture was then refluxed for 3 hours with continuous stirring. It was then cooled to room temperature. The drying process was as follows:

50° C.-24 hours→110° C.-5 hours→450° C.-5 hours

EXAMPLE 18
Pre-formed glass ionomer filler synthesis

A 1 l three necked flask connected with efficient stirrer, thermometer and condenser was charged with 60.0 g of G1 glass and 524 ml of demineralized water as suspension solution with continuous stirring. A 500 ml beaker was charged with 96.0 g of polyacrylic acid (PAA) (Solid matter was around 40 wt % and the degree of polymerization was approximately 1100) and 238 ml of demineralized water.

When the G1 glass has been completely dispersed, the PAA solution was added to the flask over the period of one hour.

The beaker was washed with 238 g of demineralized water and this wash liquid was added to the flask.

The reaction mixture was heated to 48°–52° C. This temperature was maintained for 3.5 hours.

The gelation time is approximately one hour.

This mixture (wet gel) was left for one night at room temperature. pH was 5.5.

This wet gel was dried for 5 days using a freeze-drier. The resultant dry gel was ground using a ball-mill to a mean diameter at 5.0 μm.

EXAMPLE 19
Pre-formed glass ionomer filler synthesis

A 1 l three necked flask connected with efficient stirrer, thermometer and condenser was charged with 60.0 g of G2 glass and 524 ml of demineralized water as suspension solution with continuous stirring A 500 ml beaker was charged with 96.0 g of polyacrylic acid (PAA) (Solid matter was around 40 wt % and the degree of polymerization was around 1100) and 238 ml of demineralized water.

When the G2 glass had completely dispersed, the PAA solution was added to the flask over one hour.

The beaker was washed with 238 g of demineralized water and this wash liquid was added to the flask.

The reaction mixture was heated to 48°–52° C. This temperature was maintained for 3.5 hours.

Gelation time was approximately one hour.

This mixture (wet gel) was left for one night at room temperature. pH was 5.0.

This wet gel was dried using a spray-drier at 115° C. The resultant hemi-dried gel was further dried for one day using a freeze-drier. There was no need for ball-milling as the mean diameter of the dry gel was 2.0 µm.

EXAMPLE 20
Pre-formed glass ionomer filler synthesis

A 1 l three necked flask connected with efficient stirrer, thermometer and condenser was charged 60.0 g of G10 glass and 524 ml of demineralized water as suspension solution with continuous stirring.

A 500 ml beaker was charged with 96.0 g of polyacrylic acid (PAA) (Solid matter was approximately 40 wt % and the degree of polymerization was approximately 1100) and 238 ml of demineralized water.

When the G10 glass had been completely suspended, the PAA solution was added to the flask over one hour. The beaker was washed with 238 g of demineralized water and this wash liquid was added to the flask. The reaction mixture was heated to 48°–52° C. This temperature was maintained for 12 hours.

The gelation time was approximately 5 hours.

This mixture (wet gel) was left for one night at room temperature, pH was 5.0.

This wet gel was frozen by refrigerator at −10° C. overnight followed by thawing at room temperature. This resulted in the wet gel being divided into cake filtrate.

After filtration, the cake was dried for 2 days using a freeze-drier. The resultant dry gel was ground to a mean diameter of 4.0 µm using a ball-mill.

EXAMPLE 21
Pre-formed glass ionomer filler synthesis

A 1 l three necked flask connected with efficient stirrer, thermometer and a condenser was charged with 96.0 g of polyacrylic acid (PAA) (Solid matter approximately 40 wt % and the degree of polymerization was around 1100) and 238 ml of demineralized water with continuous stirring. A 500 ml beaker was charged with 60.0 g of Solex.1 glass and 524 ml of demineralized water as suspension solution. When the PAA solution had been made completely uniform, the glass suspension solution was added to the flask over the period of two hours.

The reaction mixture was heated to 48°–52° C. This temperature was maintained for 3 hours.

The gelation time was approximately 2 hours.

The mixture (wet gel) was left overnight at room temperature. pH was 5.0.

This wet gel was frozen using liquid nitrogen for one hour, followed by thawing at room temperature. This resulted in the wet gel being divided into cake and filtrate.

After filtration, the cake was dried for 21 days using a freeze-drier. The resultant dry gel was ground using a jet-mill to a mean diameter of 2.5 µm.

EXAMPLE 22
Pre-formed glass ionomer filler synthesis

A 500 ml kneading machine equipped with thermometer and torque-meter was charged with 96.0 g of a copolymer (Solid matter was approximately 50 wt %, the copolymer contained the monomers acrylic acid 70 mol % and itaconic acid 30 mol %, the degree of polymerization was approximately 1000).

A 500 ml beaker was charged with 192.0 g of Solex.4 glass and 10 ml of demineralized water as suspension solution. This glass suspension solution was added to the kneading machine over the period of ten minutes.

The reaction mixture was cooled to 5° C.–7° C. This temperature was maintained for 2 hours with continuous reaction and grinding.

The gelation time was approximately 30 minutes.

This mixture was left overnight at room temperature. The resultant mixture was ground to a mean diameter of 3 µm using a vibrating-mill. After grinding, the powder was dried for 2 days using a freeze-drier. The mean diameter was approximately 2.8 µm.

EXAMPLES 23–29

Three one pack light curable cements comprising a pre-formed glass ionomer were prepared from di-(methacryloxyethyl)isophorone diurethane(IPDI-HEMA), triethylene glycol dimethacrylate (TEGDMA), 2-hydroxyethylmethacrylate (2-HEMA), 4-acryloxyethyltrimellitic acid (4-AET), di-camphorquinone (CQ), 1,3,5,-trimethylbarbituric acid (TMBA), 2,2-bis 4-(2-hydroxy-3-methacryloyloxy propoxy)phenylpropane, 2-hydroxy propyl methacrylate and pre-formed glass ionomer filler (Gel Filler) according to the formulation listed in Table 3. The glass used in the formation of the glass ionomer filler was G2.

The shear bond strength of the cements to dentin was determined using freshly extracted bovine incisors. The bovine teeth were mounted in an epoxy resin and were flat-ground into dentin to 600 grit using a water proof abrasive paper. The polished surface of the dentin was treated with Imperva Bond Dentin Primer (Shofu Inc.) in a rubbing manner for 60 seconds. After drying the teeth a separable plastic mould of 4 mm in inner diameter and 2 mm in height was fixed to the surface of the dentin. The one pack light curable cement detailed in Table 3 was filled in the mould and visible light was irradiated onto the surface for 60 seconds (Shofu Daylight Lamp II, Shofu Inc.). After removal of the mould, the obtained test specimens were immersed in water at 37° C. for 24 hours. Shear bond strength was then measured using a Shimadzu Autograph AG-5000B at a cross-head speed of 1 mm/min.

Shear bond strength of the cements to a Au alloy was also determined. The Au alloy used was casting gold alloy type IV (Super Gold Type IV, Shofu Inc.). The Au alloy specimens were cast to the approximate dimensions of 8.0 mm width by 8.0 mm in length, then mounted in an epoxy resin. One side of each specimen was ground to 600 grit, and then air-abraded with a 50-micron grit aluminum oxide (Sandblast Treatment; HI-Blaster, Shofu Inc.). All specimens were cleaned in an ultrasonic cleaner using distilled water for 5 minutes.

Impreva Bond Primer solution was applied to the prepared surface with a small brush and the sample was then air-dried. The plastic mould (inner diameter: 4 mm, height: 2 mm) was fixed to the surface of the Au alloy. The light curable cement listed in Table 3 was filled in the mould and was cured by visible light irradiation for 1 minute. The test specimens thereby obtained were immersed in water at 37° C. for 1 day and then the shear bond strength of the cements to Au alloy were measured at a cross-head speed of 1 mm/min.

Compressive strength and proportional limit of the compressive strength were measured. The light curable cement listed in Table 3 was filled in the plastic mould (inner diameter: 4 mm, height; 4 mm) and then visible light was irradiated on the surface of both top (for one min.) and bottom (for one min), respectively. The obtained test specimens were immersed in water at 37° C. for 1 day and then compressive strength and its proportional limit were measured at a cross-head speed of 1 mm/min.

Depth of cure was also measured in the same above conditions on irradiation. The results are shown in table 3.

TABLE 3

Physical Properties of one pack light curable cement comprising a pre-formed glass ionomer filler

|  | Ex 23 | Ex. 24 | Ex. 25 | Ex. 26 | Ex. 27 | Ex. 28 | Ex. 29 |
|---|---|---|---|---|---|---|---|
| Filler No. | Ex. 19 | Ex. 19 | Ex. 19 | Ex. 18 | Ex. 20 | Ex. 21 | Ex. 22 |
| Filler Contents (wt %) | 33.0 | 50.0 | 67.0 | 67.0 | 75.0 | 75.0 | 80.0 |
| Resin Contents (wt %) | 67.0 | 50.0 | 33.0 | 33.0 | 25.0 | 25.0 | 20.0 |
| Proportion of Resin Composition (wt %) | | | | | | | |
| Bis-GMA | — | — | — | 45.0 | 38.0 | 38.0 | 50.0 |
| IPDI-HEMA | 50.0 | 50.0 | 50.0 | — | — | — | — |
| TEGDMA | 38.0 | 38.0 | 38.0 | 43.0 | 47.0 | 47.0 | 35.0 |
| 2-HEMA | 5.0 | 5.0 | 5.0 | 10.0 | 8.0 | — | — |
| 2-HPMA | — | — | — | — | — | 8.0 | 7.8 |
| 4-AET | 5.0 | 5.0 | 5.0 | — | 5.0 | 5.0 | 5.0 |
| CQ | 0.7 | 0.7 | 0.7 | 0.7 | 0.7 | 0.7 | 0.8 |
| TMBA | 1.3 | 1.3 | 1.3 | 1.3 | 1.3 | 1.3 | 1.4 |
| Compressive Strength (MPa) | 301.1 | 315.7 | 330.3 | 288.5 | 293.2 | 287.6 | 355.7 |
| Proportional Limit (Mpa) | 184.2 | 187.3 | 193.2 | 160.7 | 161.1 | 163.1 | 193.2 |
| Shear Bond Strength (Mpa) | | | | | | | |
| to Dentin | 12.9 | 10.4 | 11.8 | 7.5 | 11.3 | 11.7 | 12.0 |
| to Au Alloy | 5.0 | 10.9 | 7.8 | 4.3 | 7.5 | 6.9 | 8.1 |

Note:
1. Bis-GMA: 2,2-bis-4-(2-hydroxy-3-methacryloyloxypropoxy)phenyl propane;
2. IPDI-HEMA: Di-(methacryloxyethyl)isophorone diurethane;
3. TEGDMA: Triethyleneglycol dimethacrylate;
4. 2-HEMA: 2-Hydroxyethylmethacrylate;
5. 2-HPMA: 2-Hydroxypropylmethacrylate;
6. 4-AET: 4-Acryloxyethyltrimellitic acid;
7. CQ: dl-Camphorquinone;
8. TMBA: 1,3,5-trimethylbarbituric acid

EXAMPLE 30

The process of Example 18 was repeated to produce a dry gel having a mean diameter of 5.0 μm. The ground gel was mixed with sodium fluoride having a particle size of 5.0 μm in an appropriate mixer.

EXAMPLE 31–42

One pack light curable cements having formula shown in tables 4 and 5 were prepared using pre-formed glass ionomer filler of Example 19. Shear bond strength of the each cement to bovine dentin and to Au alloy was determined by means of above mentioned method. The reselts are shown in tables 4 and 5.

TABLE 4

Adhesive Properties of One Pack Light Curable Cement Comprising A Pre-Formed Glass Ionomer

|  | Ex. 31 | Ex. 32 | Ex. 33 | Ex. 34 |
|---|---|---|---|---|
| pre-formed glass ionomer filler (wt %) | 50 | 50 | 50 | 50 |
| resin (wt %) | 50 | 50 | 50 | 50 |
| proportion of resin composition (wt %) | | | | |
| 1. Copolymers/Oligomers | 50% BIS-GMA | 25% IPDI-HEMA 25% BIS-GMA | 70% IPDI-HPMA | 60% IPDI-HPMA |
| 2. Diluents | 38% TEGDMA | 38% TEGMDA | 18% TEGDMA | 28% TEGDMA |
| 3. Hydrophilic Structures | 5% 2-HEMA | 5% 2-HEMA | 5% 2-HEMA | 5% 2-HEMA |
| 4. Adhesion Promoters | 5% 4-AET | 5% 4-AET | 5% 4-AETA | 5% phenyl-P |
| 5. Light Cure Catalysts | 0.7% CQ 1.3% TMBA | 0.7% CQ 1.3% TMBA | 0.5% CQ 1.5% DBTDL | 0.5% CQ 1.4% TMBA 0.1% BBA |
| Shear Bond Strength (Mpa) | | | | |
| to Denthin | 9.8 | 11.1 | 6.9 | 12.9 |
| to Au Alloy | 3.3 | 8.9 | 4.8 | 4.0 |

|  | Ex. 35 | Ex. 36 | Ex. 37 |
|---|---|---|---|
| pre-formed glass ionomer filler (wt %) | 50 | 50 | 50 |
| resin (wt %) | 50 | 50 | 50 |

TABLE 4-continued

| proportion of resin composition (wt %) | | | | | | |
|---|---|---|---|---|---|---|
| 1. Copolymers/ Oligomers | 60% | IPDI-HHMA | 60% | IPDI-HHMA | 60% | IPDI-HHMA |
| 2. Diluents | 28% | TEGDMA | 30% | TEGDMA | 28% | TEGDMA |
| 3. Hydrophilic Structures | 5% | 2-HEMA | 7.5% | 2-HEMA | 8% | 2-HEMA |
| 4. Adhesion Promoters | 5% | 4-MHT | 0.5% | PMDM | 1% | NPG-GMA |
| 5. Light Cure Catalysts | 0.5% 1.5% | CQ TMBA | 0.5% 1.5% | CQ TMBA | 0.5% 1.5% | CQ TMBA |
| Shear Bond Strength (Mpa) | | | | | | |
| to Denthin | | 9.6 | | 8.6 | | 8.8 |
| to Au Alloy | | 6.1 | | — | | — |

Note:
1. A pre-formed glass ionomer filler of Ex. 19 content is 50 wt %;
2. BIS-GMA: 2,2-bis 4-(2-hydroxy-3-methacryloyloxypropoxy)phenyl propane;
3. IPDI-HEMA: Di-(methacryloxyethyl)isoprhorone diurethane;
4. IPDI-HPMA: di-(methacryloxypentyl)isophorone diurethane;
5. IPDI-HHMA: di-(methacryloxyhexyl)isophorone diurethane;
6. PMDN: An adduct of promelitic acid anhydride and 2-hydroxyethylmethacrylate;
7. 4-AET: 4-acryloxyethyltrimellitic acid;
8. 4-AETA: 4-acryloxyethyltrimellitic acid anhydride;
9. 4-MHT: 4-methacryloxyhexyltrimellitic acid;
10. Phenyl-P: (2-methacryloxyethylphenyl) phosphoric acid;
11. NPG-GMA: N-phenylglycine-glycidilmethacrylate;
12. DBTDL: dibutyl-tin-dilaurate;
13. BBA 5-butylbarbituric acid;
14. CQ: dl-camphorquinone;
15. 2-HEMA: 2-hydroxyethylmethacrylate;
16. TEGDMA: triethyleneglycoldimethacrylate;
17. TMBA: 1,3,5-trimethylbarbituric acid;
18. Shear Bond Test: same manner in Ex 23–25

TABLE 5

Examples of One Pack Light Curable Cement Comprising Pre-Formed Glass Ionomer Cell Filler

| | Ex. 38 | Ex. 39 | Ex. 40 | Ex. 41 | Ex. 42 |
|---|---|---|---|---|---|
| pre-formed glass resin (wt %) | 50 50 | 50 50 | 20 80 | 60 40 | 40 60 |
| 4-AET | 5 | 5 | 5 | 5 | 8.5 |
| TMHDI-HEMA | 55 | 55 | 52 | 52 | 40 |
| TEGDMA | 30 | 30 | 35 | 35 | 40 |
| 2-HEMA | 5 | 3.5 | 3 | 3 | 10 |
| MTMSi | 3 | 3 | 3 | 3 | — |
| CQ | 0.5 | 0.5 | 0.5 | 0.5 | 0.5 |
| DMAEM | 0.75 | 1.5 | 1.5 | 1.5 | 0.9 |
| TMBA | — | 1.5 | — | — | — |
| DBTDL | 0.75 | — | — | — | — |
| CEBA | — | — | — | — | 0.1 |
| Shear Bond Strength (Mpa) | | | | | |
| to Dentin | 10.2 | 7.3 | 9.6 | 7.5 | 11.7 |

1. TMHDI-HEMA: di-(methacryloxyethyl)trimethlhexamethylene diurethane
2. MTMSi: γ-methacryloxyethyltrimethoxy silane
3. DMAEM: N,N-dimethacryloxyethyl methacrylate
4. TMBA: 1,3,5-trimethylbarbituric acid
5. DBTDL: dibutyl-tin-dilaurate
6. CEBA: 1-cyclohexyl-5-ethylbarbituric acid

EXAMPLE 43–46

Four one-pack light curable cements were prepared by mixing and adduct of 2,2,4-trimethylhexamethylene diisocyanate and 2-hydroxyethylmethacrylate in 1:2 molar ratio (50 parts by weight), triethyleneglycol dimethacrylate (30 parts by weight), ethyleneglycoldimethacrylate (5 parts by weight), 2-hydroxyethylmethacrylate (10 parts by weight), gamma-methacryloxyethyltrimethoxy silane (3 parts by weight), 4-acryloxyethyltrimellitic acid (5 parts by weight), camphorquinone (0.8 parts by weight), N,N-dimethylaminoethylmethacrylate (0.5 parts by weight), di-n-octyl-tin-dilaurate (0.1 parts by weight) and pre-formed glass ionomer filler (Gel Filler: 5–30 wt % in resin matrix) according to the formulation listed in Table 6. The pre-formed glass ionomer filler used is described in Example 19.

Shear bond strength of the light curable cement to dentin was determined using freshly extracted bovine incisors. The bovine teeth were mounted in epoxy resin and were flat-grounded into dentin to 600 grit by using a water proof abrasive paper. The polished surface of the dentin was treated with Imperva Bond Dentin Primer (Shofu Inc.) in a rubbing manner for 60 seconds. After drying the teeth, the one pack light curable cements detailed in Table 6 were applied to the surface of the bovine dentin and then visible light was irradiated onto the surface for 60 seconds (Shofu Daylight Lamp II, Shofu Inc.). A separable plastic mould of 4 mm in inner diameter and 2 mm in height was fixed to the surface of the bovine dentin. A light-cure composite resin (Shofu LITE-FIL A, Shofu Inc.) was filled in the plastic mould, then visible light was irradiated onto the surface for 30 seconds (Shofu Daylight Lamp II, Shofu Inc.). After removal of the mould, the obtained test specimens were immersed in water at 37° C. for 24 hours and shear bond strength was then measured using a Shimadzu Autograph AG-5000B at a cross-head speed of 1 mm/min.

TABLE 6

Adhesive Properties of One Pack Light Curable Cement Comprising a Pre-formed Glass Ionomer Filler

| | Ex. 43 | Ex. 44 | Ex. 45 | Ex. 46 |
|---|---|---|---|---|
| Filler Contents (wt %) | 5 | 10 | 20 | 30 |
| Resin Contents (wt %) | 95 | 90 | 80 | 70 |
| Shear Bond Strength (Mpa) | 12.4 | 13.2 | 14.5 | 15.6 |

EXAMPLES 47, 48; COMPARATIVE EXAMPLES 1, 2

Dental cement compositions of Examples 47, 48 and Comparative Examples 1, 2 were prepared according to respective compositions and ingredient proportions as shown in Table 7, and respective samples were tested as to fluoride-ion release and extent of solubility.

again immersed in 35 ml of fresh deionized water and, upon the lapse of a next specified time period, measurement was made likewise of the fluoride ion concentration in the water. Further again, the specimens were immersed in fresh deionized water. From the value of each measurement of fluoride ion concentration was determined the quantity of fluoride ion release for each 1 g of the fluorine source content of each specimen. Values of fluoride ion release thus determined

TABLE 7-1

Prepared compositions and fluorine content of each example

|  | proportion of raw glass (wt %) | proportion of polyalkenoic acid (wt %) | filler content in cement (wt %) | resin formulation (wt %) | | resin content in cement (wt %) | fluorine content in cement (wt %) |
|---|---|---|---|---|---|---|---|
| Example 47 | Example 2 [G2] 37.2 | PAA 29.8 | 67 | IPDI-HEMA<br>TEGDMA<br>2-HEHA<br>4-AET<br>CQ<br>TMBA | 50<br>38<br>5<br>5<br>0.7<br>1.3 | 33 | 7.63 |
| Example 48 | Example 2 [G2] 22.2 | PAA 17.8 | 40 | TMHDI-HEMA<br>TEGDMA<br>2-HEMA<br>4-AET<br>CQ<br>DMAEM<br>CEBA | 40<br>40<br>10<br>8.5<br>0.5<br>0.9<br>0.1 | 60 | 4.56 |
| Comparative Example 1 | Example 2 [G2] | — | 67 | IPDI-HEMA<br>TEGDMA<br>2-HEMA<br>4-AET<br>CQ<br>TMBA | 50<br>38<br>5<br>5<br>0.7<br>1.3 | 33 | 13.7 |
| Comparative Example 2 | Example 2 [G2] 67 | PAA 40 wt % solution 33 | — | — | | — | 13.7 |

Preparation of Test Specimens

Examples 47, 48 and Comparative Example 1: A composition was filled in a mold and was subjected to light exposure. Immediately the content was kept under the temperature and humidity conditions of 37°±1° C., and 90–100% for 10 minutes, being then removed from the mold.

Comparative Example 2: Materials were mixed in a powder/liquid ratio of 2:1 and kneaded in a conventional manner, and the kneaded mixture was filled in a mold. The content was kept under the same conditions as mentioned above for 2 minutes and 30 seconds. The resulting specimen was then removed from the mold.

Measuring Tests for Fluoride Ion Release

A test specimen was sized 4 mm$\phi$ with a thickness of 1 mm. Ten specimens were immersed in 35 ml deionized water and kept therein at 37°±1° C. After lapse of a specified time period, the specimens were removed from the water and measurement was made of the fluoride ion concentration in the water by using an ion electrode. The specimens were were added up to find a total quantity of fluoride ion release. Measurements were made in the following time sequence: after one day, after four days, after one week, after two weeks, and after one month. The results of the measurements are shown in Table 7-2 and FIG. 1.

Solubility Tests

Figure 2:
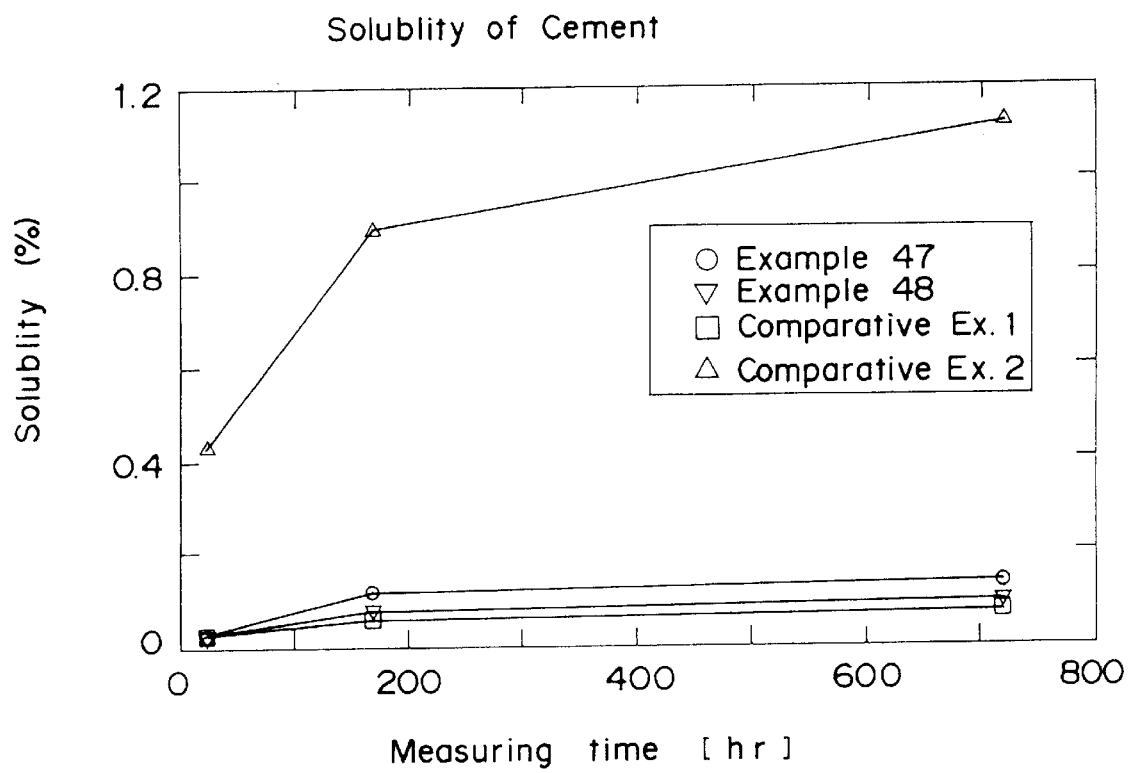
FIG. 2 is a graph showing the results of EXAMPLE 48.

A test specimen was sized 16 mm$\phi$ with a thickness of 1 mm. Immediately after its removal from a mold, the specimen was suspended in deionized water as contained in a suitable container and was kept in that condition at 37°±1° C. After having been allowed to stand for a specified time period, the specimen was taken out and the deionized water therein was evaporated, thereby to determine a remaining solid content, which was compared with the mass of the original specimen to determine the percentage of degradation. Tests were made separately for specimens immersed in deionized water for one day, for one week, and for one month, respectively. The results of the tests are shown in Table 7-2 and FIG. 2.

TABLE 7-2

Fluoride ion release and solubility of each example

|  | fluoride ion release per 1 g of of fluorine resource ($\mu$g/g) | | | | | solubility of cement (%) | | |
|---|---|---|---|---|---|---|---|---|
|  | 1 day later | 4 days later | 7 days later | 14 days later | 30 days later | 1 day later | 7 days later | 14 days later |
| Example 47 | 2490 | 5110 | 6970 | 8930 | 10350 | 0.027 | 0.114 | 0.135 |

TABLE 7-2-continued

Fluoride ion release and solubility of each example

| | fluoride ion release per 1 g of of fluorine resource (μg/g) | | | | | solubility of cement (%) | | |
|---|---|---|---|---|---|---|---|---|
| | 1 day later | 4 days later | 7 days later | 14 days later | 30 days later | 1 day later | 7 days later | 14 days later |
| Example 48 | 1210 | 2210 | 3180 | 4850 | 6340 | 0.026 | 0.078 | 0.096 |
| Comparative Example 1 | 88 | 168 | 263 | 328 | 365 | 0.025 | 0.056 | 0.071 |
| Comparative Example 2 | 1740 | 3460 | 4390 | 5870 | 7910 | 0.430 | 0.900 | 1.120 |

EXAMPLE 47 (USED THE RESIN FORMULATION OF EXAMPLE 25)

In this Example, the sample was prepared from the same glass that was used in Comparative Example 1. Thus, the improved fluoride ion can be seen to be due to the presence of pre-formed glass ionomer filler. The solubility of the composition was seen to be relatively low level.

EXAMPLE 48 (USED THE RESIN FORMULATION OF EXAMPLE 42)

Here lower fluoride ion release was predicted for the high content of resin but it is to be noted that the fluoride ion release obtained in this Example is greater than that of Comparative Example 1. The difference between the fillers which contains a lot of fluoride as glass powder and pre-formed glass ionomer filler. The solubility of this Example is thought to be low level due to the "rich" resin.

COMPARATIVE EXAMPLE 1

The raw glass described in Example 2 (G2) was milled and used as filler. The composition was based on Example 25 (ie. the pre-formed glass ionomer filler shown in Example 19: resin=2:1). The glass of Example 2 (G2), the particle size of which was the same as that of the pre-formed glass ionomer filler of Example 47, was used as filler. Despite the composition of Comparative Example 1 containing many fluorines, the release in this Example was substantially zero. The solubility was low level.

COMPARATIVE EXAMPLE 2

The glass powder of Example 2 was mixed with the liquid for cement which is commonly used in known glass ionomer cement. The main composition of the liquid was an aqueous solution of PAA. The fluoride ion release would seem to be reasonably high level however the solubility of the composition was extremely high and unstable.

EXAMPLE 49

Preparation of self-adhesive light curable fissure sealant.

Four one-pack self-adhesive light curable fissure sealants were prepared by using a kneading machine. The formulations are set out in Table 8. The pre-formed glass ionomer filler is made by the method described in Example 18.

Tensile bond strength of self-adhesive light curable fissure sealant to enamel was determined using freshly extracted bovine incisors. The bovine teeth were ground flat into enamel to 600 grit using a water proof abrasive paper. After the polished surface of the enamel had dried, a separable plastic mould having an inner diameter of 4 mm and a height of 2 mm was fixed to the surface of the bovine enamel. The plastic mould was then filled with one-pack self-adhesive light curable fissure sealant. The sealant was cured using visible light (Shofu Daylight Lamp II, Shofu Inc.) for ten seconds.

After removal of the mould, a SUS-rod of 6 mm in diameter was fixed to the cured fissure sealant using IMPERVA DUAL (Shofu Inc). The obtained test specimens were immersed in water at 37° C. for 24 hours, then tensile bond strength was measured using Shimadzu Autograph AG-5000B. A cross-head speed of 1 mm/min was used. Fluoride ion release was also measured. The measurement method of fluoride ion release is discussed above. The following results were obtained.

TABLE 8

Composition of Self-adhesive Light Curable Fissure Sealant Comprising a Pre-formed Glass Ionomer Filler.

| | wt % | | | |
|---|---|---|---|---|
| | Ex.49-1 | Ex.49-2 | Ex.49-3 | Ex.49-4 |
| Bis-GMA | 20.0 | 19.7 | 18.7 | 18.4 |
| EGDMA | 22.3 | 22.0 | 20.8 | 20.5 |
| 2-HEMA | 22.0 | 21.7 | 20.5 | 20.2 |
| 4-AET | 10.0 | 9.9 | 9.3 | 9.2 |
| CQ | 0.2 | 0.3 | 0.2 | 0.3 |
| DNOTLA | 0.5 | 1.5 | 0.5 | 1.5 |
| Ex.18 filler | 25.0 | 25.0 | 30.0 | 30.0 |

TABLE 9

Adhesive and Fluoride Release Properties of Self-adhesive Light Curable Fissure Sealant Comprising a Pre-formed Glass Ionomer Filler.

| | Ex.49-1 | Ex.49-2 | Ex.49-3 | Ex.49-4 |
|---|---|---|---|---|
| Adhesive Strength (Mpa) | 10.5 | 10.9 | 11.0 | 13.7 |
| Fluoride ion release (μg/g) 24 hours after | 2850 | 3264 | 2750 | 2600 |

-NOTE-

| | |
|---|---|
| Bis-GMA: | 2,2-bis 4-(2-hydroxy-3-methacryloyloxypropoxyphenyl) propane |
| EGDMA: | Ethyleneglycol-dimethacrylate |
| 2-HEMA: | 2-hydroxyethylmethacrylate |
| 4-AET: | 4-acryloxyethyltrimellitic acid |
| CQ: | dl-camphorquinone |
| DNOTLA: | n-dioctyl-tin-dilaurate |

EXAMPLE 50

Preparation of One-pack Self-adhesive Light Curable Cements.

Four one-pack self-adhesive light curable cements were prepared using a kneading machine. The formulations are listed in Table 10 and the pre-formed glass ionomer filler of Example 20 was used.

Tensile bond strength of self-adhesive light curable cements to enamel and dentin was determined using freshly extracted bovine incisors. The bovine teeth were ground flat into enamel and dentin to 600 grit by using a water proof abrasive paper. After the polished surface of the enamel and dentin had dried, a separable plastic mould having an inner diameter of 4 mm and a height of 2 mm was fixed to the surface of the bovine enamel and dentin.

The plastic mould was filled with one-pack self-adhesive light curable cement which was then cured by being exposure to visible light (Shofu Daylight Lamp II, Shofu Inc.) for ten seconds. After the mould was removed, a SUS-rod of 6 mm in diameter was fixed to the cured cement using IMPERVA DUAL (Shofu Inc). The obtained test specimens were immersed in water at 37° C. for 24 hours, then tensile bond strength was measured by using Autograph AG-5000B (Shimadzu Inc.). A cross-head speed of 1 mm/min was used. The fluoride ion release was also measured. The measurement method of fluoride ion release has been already described.

The results obtained are set out in Table 11.

TABLE 10

Composition of Self-adhesive Light Curable Cements Comprising a Pre-formed Glass Ionomer Filler.

|  | Ex.50-1 | Ex.50-2 | Ex.50-3 | wt % Ex.50-4 |
|---|---|---|---|---|
| Bis-GMA | 16.7 | 16.7 | 10.0 | 10.0 |
| EGDMA | 12.0 | 3.1 | 9.3 | 3.3 |
| 2-HEMA | 5.5 | 10.0 | 20.0 | 24.0 |
| 4-AET | 0.6 | 5.0 | 10.0 | 12.0 |
| CQ | 0.1 | 0.1 | 0.1 | 0.1 |
| DNOTLA | 0.6 | 0.6 | 0.6 | 0.6 |
| Ex.20 filler | 64.5 | 64.5 | 50.0 | 50.0 |

TABLE 11

Adhesive and Fluoride Ion Release Properties of Self-adhesive Light Curable Cements Comprising a Pre-formed Glass Ionomer Filler.

|  | Ex.50-1 | Ex.50-2 | Ex.50-3 | wt % Ex.50-4 |
|---|---|---|---|---|
| Adhesive strength (MPa) | | | | |
| to enamel | 0.1 | 4.3 | 5.5 | 5.7 |
| to dentin | 0.2 | 4.4 | 4.8 | 407 |
| Fluoride | | | | |
| release (µg/g) 24 hours after | 736 | 815 | 1017 | 946 |

-NOTE-

Bis-GMA: 2,2-bis 4-(2-hydroxy-3-methacryloyloxypropoxyphenyl) propane
EGDMA: Ethyleneglycol-dimethacrylate
2-HEMA: 2-hydroxyethylmethacrylate
4-AET: 4-acryloxyethyltrimellitic acid
CQ: dl-camphorquinone
DNOTLA: n-dioctyl-tin-dilaurate

EXAMPLE 51

Preparation of one-pack self-adhesive light curable bonding agent.

Four one-pack self-adhesive light curable bonding agents were prepared using a kneading machine. The formulations are listed in Table 12 and the pre-formed glass ionomer filler is made by the method described in Example 21.

Tensile bond strength of self-adhesive light curable cements to enamel and dentin was determined using freshly extracted bovine incisors. The bovine teeth were ground flat into enamel and dentin to 600 grit by using a water proof abrasive paper. After the polished surface of the enamel and dentin had dried, one-pack self-adhesive light curable cement was applied to the surface of the enamel and dentin. The cement was then cured by being exposed to visible light (Shofu Daylight Lamp II, Shofu Inc.) for 10 seconds. A separable plastic mould having an inner diameter of 4 mm and a height of 2 mm was fixed to the surface of the bovine enamel and dentin. The plastic mould was then filled with a light-cure composite resin (Shofu LITE-FIL II A, Shofu Inc.) which was cured using visible light (Shofu Daylight Lamp II, Shofu Inc.) for fifteen seconds. After removal of the mould, a SUS-rod of 6 mm in diameter was fixed to the cured LITE-FIL A using IMPERVA DUAL (Shofu Inc.). The obtained test specimens were immersed in water at 37° C. for 24 hours, then tensile bond strength was measured by using Shimadzu Autograph AG-5000B. A cross-head speed of 1 mm/min was used.

Fluoride ion release was also measured. The measurement method of fluoride ion release has already been described.

The results obtained are set out in Table 13.

TABLE 12

Composition of Self-adhesive Light Curable Bonding Agents Comprising a Pre-formed Glass Ionomer Filler.

|  | Ex. 51-1 | Ex 51-2 | Ex. 51-3 | wt % Ex. 51-4 |
|---|---|---|---|---|
| Bis-GMA | 40.3 | 27.3 | 24.3 | 19.3 |
| EGDMA | 40.0 | 40.0 | 30.0 | 15.0 |
| 2-HEMA | 10.0 | 15.0 | 20.0 | 30.0 |
| 4-AET | 4.0 | 7.0 | 10.0 | 15.0 |
| CQ | 0.2 | 0.2 | 0.2 | 0.2 |
| DNOTLA | 0.5 | 0.5 | 0.5 | 0.5 |
| Ex.21 filler | 5.0 | 10.0 | 15.0 | 20.0 |

TABLE 13

Adhesive and Fluoride Release Properties of Self-adhesive Light Curable Bonding Agents Comprising a Pre-formed Glass Ionomer Filler.

|  | Ex. 51-1 | Ex. 51-2 | Ex. 51-3 | Ex. 51-4 |
|---|---|---|---|---|
| Adhesive Strength (MPa) | | | | |
| to enamel | 8.0 | 9.3 | 10.9 | 10.7 |
| to dentin | 7.2 | 9.0 | 9.7 | 10.2 |
| Fluoride ion | | | | |
| release (µg/g) 24 hours after | 2658 | 2400 | 2500 | 2400 |

-NOTE-

Bis-GMA: 2, 2-bis 4-(2-hydroxy-3-methacryloyl oxypropoxyphenyl) propane
EGDMA: Ethyleneglycol-dimethacrylate
2-HEMA: 2-hydroxyethylmethacrylate
4-AET: 4-acryloxyethyltrimellitic acid
CQ: dl-camphorquinone
DNOTLA: n-dioctyl-tin-dilaurate

EXAMPLE 52

A pre-formed glass ionomer filler obtained in Example 20 was dispersed in 50 g of deionized water. The concentration of fluoride ions released from 0.0002–2.0 g of the filler was measured by ion electrodes, the results of which were as shown in the table below. For comparison purposes, fluoride ion concentration was also measured with respect to sodium chloride.

TABLE 14

|  | filler (g) | NaF (g) | Fluoride ion concentration (ppm) |
|---|---|---|---|
| Example 52-1 | 2.0 | — | 39.2 |
| Example 52-2 | 0.2 | — | 13.1 |
| Example 52-3 | 0.02 | — | 3.1 |
| Example 52-4 | 0.002 | — | 0.6 |
| Example 52-5 | 0.0002 | — | 0.2 |
| Comparative Example 3-1 | — | 2.0 | 15300 |
| Comparative Example 3-2 | — | 0.2 | 1720 |
| Comparative Example 3-3 | — | 0.02 | 179 |
| Comparative Example 3-4 | — | 0.002 | 18 |

(Note) Respective fillers were dispersed in 50 g of deionized water.

As is apparent from the above tabulated results, even when the concentration of the filler of the invention is lowered to 1/10 and further to 1/100, fluoride ion concentrations are at 1/3 and 1/10 levels respectively. This shows that when fluoride ions are consumed, their supply is replenished. Thus, it may be said that the supply and consumption of fluoride ions is in an equilibrium state. In contrast, no such tendency was found in Comparative Examples 3-1 to 3-4.

Further, the filler of the invention started fluoride ion release in a very short time. It was also witnessed that when the filler which once released fluoride ions was dried and again dispersed in water for measurement of fluoride ion concentration, a measurement value about comparable to the previously measured value was obtained. It is apparent from the above that fluorine release by the filler of the invention largely takes the form of exchange of ligands, so that the filler exhibits stable and fluoride-ion release sustainedly in the presence of water with little or no dissolution or degradation involved. In contrast, no such tendency was found in Comparative Examples 3-1 to 3-4 wherein the fluorine compound showed an elution behavior.

EXAMPLE 53

Eight kinds of pre-formed glass ionomer fillers were prepared using the glass of Example 6, which were examined as to their physical properties and fluoride-ion release capabilities.

The pre-formed glass ionomer fillers were produced in the following ways.

Examples 53-1 to 53-3: Reaction was carried out in the same way as in Example 18, and the reaction product was freeze dried under vacuum.

Example 53-4: Materials were mixed by a kneader for reaction under low temperature conditions. The reaction mixture was freeze dried under vacuum.

Example 53-5: Materials were subjected to reaction at 3 kgf/cm$^2$ in an autoclave under a nitrogen atmosphere. The reaction product was freeze dried.

Examples 53-6 to 53-10: Materials were kneadingly mixed by hand in small quantities on a mixing plate or in a beaker. The mixture was then freeze dried under vacuum. (The powder/liquid ratio of the filler of Example 53-6 was virtually same as that of commercially available glass ionomer cement.)

Measurement of Fluoride-Ion Release Capability

Two grams of filler was dispersed in 50 g of deionized water and the dispersion was stirred for one hour. Then, 30 ml of the dispersion was sampled. The sample was subjected to centrifugal sedimentation at 4000 rpm for 30 minutes, which was filtered with a membrane filter of 0.1 μm, as required, to obtain a supernatant liquid, 24 ml of which liquid was used as a test liquid. The test liquid was loaded with 3 ml of a buffer solution, as an ion intensity adjust agent. Measurement was made by using ion electrodes. A fluoride-ion concentration was determined from a previously drawn calibration curve, which concentration was taken as a fluoride-ion release capability. All measurements were carried out at 23° C. and the deionized water and the buffer solution were kept in the same concentration as aforesaid. The results are shown in Table 15. The quantity of fluoride-ion release represents a fluoride-ion release capability for 1 g of sample.

As may be apparent from Table 15, the fluoride-ion release capability is provided through the presence of excess water. It is also noted that pore volume is controllable according to the intended object, because it may be largely varied according to the mixing ratio of fluorine-containing glass, polyalkenoic acid and water.

TABLE 15

| Physical properties of preformed glass ionomer filler | | | | | | | | | | | |
|---|---|---|---|---|---|---|---|---|---|---|---|
|  | Ex. 53-1 | Ex. 53-2 | Ex. 53-3 | Ex. 53-4 | Ex. 53-5 | Ex. 53-6 | Ex. 53-7 | Ex. 53-8 | Ex. 53-9 | Ex. 53-10 | Com. Ex. 4 |
| Filler Composition | | | | | | | | | | | |
| Example 6 glass | 60 g | 60 g | 60 g | 60 g | 60 g | 2 g | 2 g | 2 g | 2 g | 2 g | 2 g |
| 40% acrylic acid aqueous solution | 150 g | 150 g | 150 g | 120 g* | 150 g | 1 g | 0.2 g* | 0.02 g* | 0.001 g* | 40 g* | 0 g |
| Deionized water | 1110 g | 750 g | 270 g | 0 g | 2310 g | 0 g | 0.2 g | 0.2 g | 0.2 g | 0 g | 0 g |
| Glass: polyacrylic acid: water (weight ratio) | 1:1:10 | 1:1:7 | 1:1:3 | 1:1:1 | 1:1:20 | 4:0.8:1.2 | 1:0.1:0.15 | 1:0.01:0.11 | 1:0.0005:0.1 | 1:10:10 | 2:0:0 |

TABLE 15-continued

Physical properties of preformed glass ionomer filler

| | Ex. 53-1 | Ex. 53-2 | Ex. 53-3 | Ex. 53-4 | Ex. 53-5 | Ex. 53-6 | Ex. 53-7 | Ex. 53-8 | Ex. 53-9 | Ex. 53-10 | Com. Ex. 4 |
|---|---|---|---|---|---|---|---|---|---|---|---|
| Physical properties of filler | | | | | | | | | | | |
| Fluoride-ion release ($\mu$g/g) | 1100 | 1100 | 940 | 870 | 1050 | 690 | 560 | 340 | 210 | 500 | 130 |
| Bulk density | 3.0 | 3.0 | 2.9 | 2.8 | 5.5 | 1.9 | 1.4 | 1.1 | 1.0 | 1.5 | 1.0 |
| Pore volume (BET process) (ml/g) | 0.25 | 0.24 | 0.23 | 0.14 | 1.20 | 0.04 | 0.02 | 0** | 0** | 0.04 | 0 |

*: 50% aqueous solution of polyacrylic acid.
**: Not completely reduced to 0 (=0).

EXAMPLE 54
Surface Treatment of Pre-formed Glass Ionomer Filler

| | |
|---|---|
| filler of Example 19 | 165 parts |
| γ-methacryloxypropyl trimethoxysilane | 15 parts |
| Ethyl alcohol | 10 parts |

The filler obtained in Example 19 and an alcohol solution of aforesaid silane treating agent were mixed together under agitation while the latter being sprayed over the former, and the mixture was pressurized to 5 kgf/cm² with nitrogen at 85° C. for one hour. Then, the pressurized mixture was dried under vacuum at 40° C. for 12 hours.

The silane treated pre-formed glass ionomer filler thus obtained and an treated pre-formed glass ionomer filler were respectively added in the amount of 10 wt % to the adhesive light cure type bonding agent of Example 51, and their respective bonding characteristics were thereby measured. The measurement results are shown in Table 16.

TABLE 16

| Tensile strength (MPa) | to Enamel | to Dentin |
|---|---|---|
| Silane treated | 11.0 | 10.0 |
| Untreated | 9.5 | 9.0 |

EXAMPLE 55

The pre-formed glass ionomer filler obtained in Example 20 was mixed with silane treated filler A (55 parts by weight), silane treated silica (25 parts by weight), silane treated barium sulfate (20 parts by weight), 1-cyclohexyl-5-ethyl barbituric acid (CEBA) (1.0 parts by weight), and N,N-di(hydroxyethyl)-p-toluidine (N,N-DEPT) (0.5 parts by weight) for preparation of a powder material.

A liquid material was prepared by mixing together di-(methacryloxyethyl) trimethylhexamethylene diurethane (TMHDI-HEMA) (50 parts by weight), 2-hydroxyethyl methacrylate (2-HEMA) (35 parts by weight), trimethylhexamethylene dimethacrylate (TEGDMA) (10 parts by weight), 4-acroloxyethyl trimellitic acid (4-AET) (5 parts by weight), benzoyl peroxide (BPO) (0.3 parts by weight), and butylated hydroxytoluene (BHT) (0.08 parts by weight).

Silane treatment of the filler was carried out in the following procedure: 100 parts by weight of the filler was mixed with y-methacryloxypropyl trimethoxysilane (7 parts by weight) and ethyl alcohol (20 parts by weight), and the mixture was pressurized to 5 kgf/cm² with nitrogen and was caused to undergo a coupling reaction at 85° C. for one hour. Thereafter, the solvent was removed under reduced pressure. The filler A was thus obtained. Silane treatment of silica and that of barium sulfate were carried out according to conventional acetic acid method. That is, the same silane coupling agent as was used in the silane treatment of the filler (3 parts by weight relative to 100 parts by weight of the filler) was used as such, and coupling reaction was carried out at 130° C. for 30 minutes.

The powder material and liquid material prepared as above described were kneadingly mixed in the ratio of 3.0/1.0, and the mixture became cured in 3.0 minutes. The cured material exhibited a compressive strength of 1783 kgf/cm² and an Ni—Cr interalloy tensile bond strength of 382 kgf/cm². Also, the cured material exhibited a fluoride-ion release with a fluoride-ion concentration of 94 $\mu$g/g. Where filler A was replaced with a silane-treated silica of same quantity, the resulting cured material could only release fluoride ions with a fluoride-ion concentration of less than 1 $\mu$g/g. Further, camphor quinone (CQ) (0.8 parts by weight) was added to the above mentioned liquid material, and the resulting mixture was kneadingly mixed with the powder material in manner as above said, which was then subjected to visible light exposure by Grip Light II (Shofu Inc.) for 30 seconds. In this case, the concentration of fluoride ions released from the cured material obtained was 77 $\mu$g/g.

From the foregoing results, it was found that dental compositions, such as composite resins, core build-up, and dental adhesive resin cement, could be made capable of fluoride-ion release sustainedly by incorporating the filler of the invention therein through chemical polymerization and dual cure.

EXAMPLE 56

Paste A was prepared by mixing together the pre-formed glass ionomer filler obtained in Example 21 which was treated with silane into filler B (55 parts by weight), a silane-treated colloidal silica (5 parts by weight), 2,2-bis [4-hydroxy-3-methacryloxypropoxy) phenyl] propane (BIS-GMA) (20 parts by weight), 2-HEMA (15 parts by weight), TEGDMA (5 parts by weight), and N-DEPT (0.4 parts by weight).

Paste B was prepared by mixing together the pre-formed glass ionomer filler obtained in Example 21 which was treated with silane into filler B (55 parts by weight), a silane-treated colloidal silica (5 parts by weight), 2,2-bis

[4-hydroxy-3-methacryloxypropoxy) phenyl] propane (BIS-GMA) (20 parts by weight), 2-HEMA (15 parts by weight), TEGDMA (5 parts by weight), 4-AET (5 parts by weight), CQ (0.6 parts by weight), and BPO (0.6 parts by weight).

Pastes A and B thus prepared were kneadingly mixed in equal quantities, and curing occurred in 3.5 minutes. After being subjected to photopolymerization through exposure to light from Daylight Lamp II, the cured material exhibited a compressive strength of 2106 kgf/cm². The cured material exhibited a fluoride-ion release capability with a fluoride ion concentration of 114 μg/g. Where filler B was replaced with silane-treated silica, the cured material could only release fluoride ions with a fluoride-ion concentration of less than 1 μg/g.

From the foregoing results, it was found that dental compositions, such as paste & paste type dual cure composite resins, fissure sealant, root surface coatings, and dental adhesive resin cement, could be made capable of fluoride-ion release by incorporating the filler of the invention therein.

EXAMPLE 57

Paste D was prepared by mixing together the pre-formed glass ionomer filler obtained in Example 21 which was silane treated to give filler B (50 parts by weight), a glass filler for glass ionomer cement (45 parts by weight), silane-treated colloidal silica (5 parts by weight), di-(methacryloxy ethyl) trimethylhexamethylene diurethane (TMHDI-HEMA) (5 parts by weight), 2-hydroxyethyl methacrylate (2-HEMA) (40 parts by weight), trimethylhexamethylene dimethacrylate (TEGDMA) (1 parts by weight), 4-acryloxyethyl trimellitic acid (4-AET) (45 parts by weight), Benzoyl peroxide (BPO) (0.08 parts by weight), and camphorquinone (CQ) (0.7 parts by weight).

Paste E was prepared by mixing together silane treated silica (30 parts by weight), silane treated barium sulfate (8 parts by weight), silane treated molten silica (6 parts by weight), silane treated colloidal silica (1 parts by weight), polyacrylic acid (50 parts by weight), 1,3,5-trimethyl barbituric acid (TMBA) (3 parts by weight), N,N-di (hydroxyethyl)-p-toluidine (N,N-DEPT) (0.5 parts by weight), and distilled water (50 parts by weight).

Pastes D and E thus prepared were kneadingly mixed in equal quantities, and curing occurred in 5.0 minutes. After being subjected to photopolymerization through exposure to light from Daylight Lamp II, the cured material exhibited a compressive strength of 644 kgf/cm². Further, the cured material exhibited a shear bonding strength of 58.7 kgf/cm² relative to a bovine dentin treated with Imperva Bond Dentin Primer. The cured material exhibited a fluoride-ion release capability with a fluoride ion concentration of 448 μg/g.

From the foregoing results, the fluoride-ion sustained release pre-formed glass ionomer filler of the invention has been found to be useful for application to dental compositions, such as glass ionomer cement, composite resins, fissure sealant, dental material for core build-up, dental lining material, temporary sealing material, root canal filling agent, root-surface coating material, and dental bonding resin cement, which can be made capable of fluoride-ion release through paste & paste type cement cure reaction+ chemical polymerization+photopolymerization (tri-cure).

EXAMPLE 58

A pre-formed glass ionomer filler prepared according to the method of Example 19 using the glass (G7 glass) of Example 7 was incorporated into a zinc phosphate cement.

The zinc phosphate cement used was comprised of the following cement powder material A and cement liquid material A, which ingredients were mixed and cured.

| Composition of cement powder material A (wt %) | |
|---|---|
| Zinc oxide | 87.5 |
| Magnesiuxn oxide | 10 |
| Bismuth subnitrate | 2.5 |

The above ingredients were mixed together and the mixture was calcined at a temperature of about 1300° C. The calcined mixture was ground into cement powder material A.

| Composition of cement liquid material A (wt %) | |
|---|---|
| Phosphoric acid (85 wt % aqueous solution) | 72.0 |
| Aluminum hydroxide | 9.0 |
| Deionized water | 19.0 |

The above ingredients were mixed together and were caused to undergo a reaction to give cement liquid material A.

Cement powder material A, cement liquid material A, and the pre-formed glass ionomer filler were mixed in the following proportions. The resulting cement was kneaded according to Japanese Industrial Standard T6602 Test Method for Zinc Phosphate Cement. Test specimens were prepared in the same way as in Comparative Example 2. Cured cement material obtained were examined as to its fluoride ion release in the manner as described in Example 47. For the purpose of comparison, a zinc phosphate cement having no pre-formed glass ionomer filler content was examined as to its fluoride ion release. The results are shown below.

| | Cement powder material A | Preformed glass ionomer filler | Cement liquid material A | Fluoride ion release* after 24 hr |
|---|---|---|---|---|
| Ex. 58 | 1.26 g | 0.14 g (10%) | 0.8 g | 10 μg/g |
| Comparative Ex. 5 | 1.4 g | 0 g | 0.5 g | 0 μg/g |

*indicates fluoride ion release per 1 g of specimen.

EXAMPLE 59

A pre-formed glass ionomer filler prepared according to the method of Example 19 using the glass (G7 glass) of Example 7 was incorporated into a carboxylate cement.

The carboxylate cement used was comprised of the cement powder material A of Example 58 and the following cement liquid material B, which ingredients were mixed and cured.

| Composition of cement liquid material B (wt %) | |
|---|---|
| Acrylic acid/3-butene-1, 2, 3 tricarboxylic acid copolymer (molecular weight 15000, 40% aqueous solution) | 93.8 |

-continued

| Composition of cement liquid material B (wt %) | |
|---|---|
| Tartaric acid | 1.2 |
| Deionized water | 5.0 |

Cement powder material A, cement liquid material B, and the pre-formed glass ionomer filler were mixed in the following proportions. Test specimens were prepared according to Japanese Industrial Standard T6606 Test Method for Dental polycarboxylate Cement. Cured cement material obtained was examined to thereby determine the compressive strength thereof. Test specimens were prepared in the same way as in Comparative Example 2, and they were examined as to fluoride ion release thereof in the manner as described in Example 47. For the purpose of comparison, a carboxylate cement having no pre-formed glass ionomer filler content was examined as to its characteristics. The results are shown below.

| | Cement powder material A | Preformed glass ionomer filler | Cement liquid material B | Compressive strength (kgf/cm²) | Fluoride ion release* after 24 hr |
|---|---|---|---|---|---|
| Ex. 59-1 | 1.9 g | 0.1 g (5%) | 1.0 g | 780 | 120 μg/g |
| Ex. 59-2 | 1.8 g | 0.2 g (10%) | 1.0 g | 785 | 122 μg/g |
| Ex. 59-3 | 1.7 g | 0.3 g (15%) | 1.0 g | 905 | 284 μg/g |
| Comparative Ex. 6 | 2.0 g | | 1.0 g | 760 | 0 g/g |

*indicates fluoride ion release per 1 g of specimen.

EXAMPLE 60

Dentifrice and rinsing agent were prepared by using the glass of Example 3 and the filler which was produced according to the method of producing the pre-formed glass ionomer filler of Example 19.

Example 60-1: Tooth Paste

| | wt % |
|---|---|
| Pre-formed glass ionomer filler | 20.0 |
| Silicic anhydride | 10.0 |
| Sorbitol liquid (60%) | 50.0 |
| Hydroxyethyl cellulose | 0.5 |
| Sodium benzoate | 0.1 |
| Sodium dodecyl sulfate | 2.0 |
| Propylene glycol | 3.0 |
| Sodium Saccharin | 0.1 |
| perfume | 1.2 |
| Refined water | balance |
| Total | 100.0 |

Example 60-2: Tooth Paste

| | wt % |
|---|---|
| Pre-formed glass ionomer filler | 25.0 |
| Dibasic calcium phosphate | 30.0 |
| Silicic anhydride | 2.0 |
| Sodium carboxymethylcellulose | 0.2 |
| Propylene glycol | 3.0 |
| Sorbitol liquid (60%) | 25.0 |
| Sodium dodecyl sulfate | 1.0 |
| Sodium paraoxybenzoate | 0.05 |

-continued

| | wt % |
|---|---|
| Sodium Saccharin | 0.2 |
| Perfume | 1.0 |
| Refined water | balance |
| Total | 100.0 |

| Fluoride ion release concentration (in ppm) | | | |
|---|---|---|---|
| Fludride-ion concentration | Example 60-1 | Example 60-2 | Comparative Ex. 5* |
| When 2 g dentifrice is dispersed in 5 ml water | 25 | 27 | 18 |
| When 2 g dentifrice is dispersed in 50 ml water | 10 | 12 | 2 |

*commercial fluorine-containing dentifrice.

Where the pre-formed glass ionomer filler is used in manner as above described, the fluoride-ion concentration is not much influenced by an oral cavity water content.

Example 60-3: Rinsing Agent

| | wt % |
|---|---|
| Pre-formed glass ionomer filler | 95.5 |
| Sodium dodecyl sulfate | 4.0 |
| Sodium Saccharin | 0.25 |
| Perfume | 0.25 |
| Total | 100.0 |

The above ingredients were compounded and mixed, and then 2 g of the mixture was packed in a tea bag. In use, the bag was immersed in 100 ml of water for about 5 minutes thereby to give a rinsing liquid. The rinsing liquid had a fluoride ion concentration of 10 ppm.

Example 60-4: Rinsing Liquid

|  | wt % |
| --- | --- |
| Pre-formed glass ionomer filler | 2.0 |
| Glycerin | 15.0 |
| Ethanol | 5.0 |
| Perfume | 0.3 |
| Sodium benzoate | 0.05 |
| Sodium dodecyl sulfate | 0.1 |
| Polyoxyethylene laurylether | 0.2 |
| Refined water | balance |
| Total | 100.0 |

The above ingredients were compounded and mixed, and then 2 g of the mixture was packed in a tea bag. In use, the bag was immersed in 100 ml of water for about 5 minutes thereby to give a rinsing liquid. The rinsing liquid had a fluoride ion concentration of 20 ppm.

INDUSTRIAL APPLICABILITY

As described above, the fluoride-ion sustained release pre-formed glass ionomer filler of the present invention is applicable to various dental compositions including, but not limited to, dental cement, dental composite resin, bonding agent, treating agent for teeth, primer for teeth treatment, bonding primer, dental adhesive resin cement, fissure sealant, orthodontics adhesive, tooth and root surface coating material, dental material for core build up, dental lining material, temporary sealing material, inter-root filling agent, capping agent, dentifrice, and rinsing agent. Thus, by adding the filler to any such dental composition it is possible to obtain a dental composition of the invention. By virtue of its fluoride-ion release capability the filler is useful for living hard tissues, such as teeth and bones, which take in fluoride ions, and is applicable for utilization in not only dental segment, but also various other segments, such as surgery, orthopaedic surgery, and plastic surgery.

As already stated, dental compositions of the present invention need not necessary be of one-paste type, but they may be of such other type as two-paste type, three-paste type, paste/liquid type, powder/liquid type, or one-liquid type.

We claim:

1. A fluoride-ion sustained release preformed glass ionomer filler comprised of a powdery reaction product of polyalkenoic acid with a fluorine-containing glass, wherein the powdery reaction product is a xerogel resulting from dehydration of a gel.

2. A pre-formed glass ionomer filler according to claim 1, wherein the mixing ratio of the polyalkenoic acid to the fluorine-containing glass is from 0.0005:1 to 10:1.

3. A pre-formed glass ionomer filler according to claim 1, wherein the polyalkenoic acid is at least one kind of polymer or copolymer with a repeating unit having a carboxyl group.

4. A pre-formed glass ionomer filler according to claim 1, wherein the filler has a particle size of from 0.01 to 100 micron and a total pore volume of from 0.04 to 2.0 cc/g.

5. A pre-formed glass ionomer filler according to claim 1, wherein the surface of the filler is treated with a silane coupling agent.

6. A method of producing a fluoride-ion sustained release pre-formed glass ionomer filler which comprises causing polyalkenoic acid and a fluorine-containing glass to react with each other in the presence of water, wherein the mixing ratio of water/(fluorine-containing glass and polyakenoic acid) is 0.1 to 10, and setting, drying and pulverizing the resulting product.

7. The method according to claim 6, wherein the mixing ratio of water:(fluorine-containing glass and polyalkenoic acid) is 0.2 to 1.5.

8. The method according to claim 6, wherein the fluorine-containing glass is prepared by a melting process or by a sol-gel process.

9. The method according to claim 6, wherein the mixing ratio of water:(fluorine-containing glass and polyalkenoic acid) is 1.0 to 10.

10. The method according to claim 9, wherein the fluorine-containing glass is prepared by a melting process or by a sol-gel process.

11. A method of producing a fluoride-ion sustained release pre-formed glass ionomer filler which comprises pulverizing a fluorine-containing glass in the presence of polyalkenoic acid and excess water, and drying the resulting product.

12. The method according to claim 11, wherein the mixing ratio of water:(fluorine-containing glass and polyalkenoic acid) is 0.4 to 10.

13. The method according to claim 11, wherein the fluorine-containing glass is prepared by a melting process or by a sol-gel process.

14. A dental composition which comprises 1 to 90 wt. % of preformed glass ionomer filler comprised of a powdery reaction product of polyalkenoic acid with a fluroine-containing glass wherein the powdery reaction product is a xerogel resulting from dehydration of a gel.

15. A dental composition according to claim 14, wherein the composition further contains a resin composition comprised of (a) a radical polymerizable compound and (b) a curing agent.

16. A dental composition according to claim 15, wherein the composition contains 0.1 to 50 parts by weight of (b) curing agent relative to a total 100 parts by weight of (a) radical polymerizable compound.

17. A dental composition according to claim 15, wherein the radical polymerizable compound is a monomer, oligomer, or polymer having more than one unsaturated double bond group selected from among (meth)acryloyl group, (meth)acrylamide group, and vinyl group.

18. A dental composition according to claim 15, wherein for (a) radical polymerizable compound the composition contains 10 to 70 wt % of a component selected from among diluents and viscosity reducers, 10 to 89 wt % of a component selected from among strength-inducing copolymers and oligomers, not more than 50 wt % of a component selected from among hydrophilic structures and hydrophilic adhesives, and 0.1 to 50 wt % of an adhesion accelerator, and for (b) curing agent, the composition contains 0.1 to 15 wt % of a curing catalyst.

19. A dental composition according to claim 15, wherein the composition is curable by photopolymerization or chemical polymerization.

20. A dental composition according to claim 15, wherein the resin composition is a light-curable composition comprised of (a) a radical polymerizable compound and (b) a light cure catalyst.

21. A dental composition according to claim 20, wherein the composition is a paste dental cement comprising a light-curable composition and a fluoride-ion sustained release pre-formed glass ionomer filler dispersed therein.

22. A dental composition according to claim 21, wherein the dental cement further comprises a hydrolyzable fluoride.

23. A dental composition according to claim 22, wherein the hydrolyzable fluoride is one selected from the group consisting of sodium fluoride, aluminum fluoride, potassium fluoride, and sodium monofluorophosphate.

24. A dental composition according to claim 21, wherein the light-curable composition contains a hydrophilic resin.

25. A dental composition according to claim 21, wherein the pre-formed glass ionomer filler has a particle size of from 0.1 to 10 μm.

26. A dental composition according to claim 15, further comprising a dental inorganic cement powder and a dental cement liquid material.

27. A dental composition according to claim 26, further comprising a resin composition comprised of (a) a radical polymerizable compound and (b) a curing agent.

28. A dental composition according to claim 26, wherein the composition is curable by any one of ionomer-glass curing, photopolymerization, and/or redox polymerization methods.

29. A dental composition according to claim 15, wherein the composition contains water or an organic solvent.

30. A dental composition according to claim 15, further comprising an organic polymer.

31. A dental composition according to claim 15, further comprising more than one component selected from the group consisting of inorganic fillers and organic composite fillers.

* * * * *